(12) United States Patent
Holt et al.

(10) Patent No.: US 9,011,778 B2
(45) Date of Patent: Apr. 21, 2015

(54) HYDROGEN SENSITIVE COMPOSITE MATERIAL, HYDROGEN GAS SENSOR, AND SENSOR FOR DETECTING HYDROGEN AND OTHER GASES WITH IMPROVED BASELINE RESISTANCE

(75) Inventors: Christopher T. Holt, Columbus, OH (US); Stephen R. Cummings, Columbus, OH (US); Scott L. Swartz, Columbus, OH (US); Lora B. Thrun, Columbus, OH (US)

(73) Assignee: NexTech Materials, Ltd., Lewis Center, OH (US)

( * ) Notice: Subject to any disclaimer, the term of this patent is extended or adjusted under 35 U.S.C. 154(b) by 0 days.

(21) Appl. No.: 11/974,520

(22) Filed: Oct. 12, 2007

(65) Prior Publication Data
US 2009/0090626 A1 Apr. 9, 2009

Related U.S. Application Data

(60) Provisional application No. 60/851,220, filed on Oct. 12, 2006.

(51) Int. Cl.
*G01N 27/00* (2006.01)
*H01M 4/38* (2006.01)
(Continued)

(52) U.S. Cl.
CPC .............. *H01M 4/383* (2013.01); *G01N 33/005* (2013.01); *H01M 8/04216* (2013.01); *Y02E 60/364* (2013.01); *Y02E 60/50* (2013.01)

(58) Field of Classification Search
USPC ........ 73/23.2–31.07; 422/82.01–98; 106/439; 502/304; 282/521.1, 509
See application file for complete search history.

(56) References Cited

U.S. PATENT DOCUMENTS 4,015,230 A * 3/1977 Nitta et al. ...................... 338/35
4,241,019 A * 12/1980 Nakatani et al. ................ 422/94
(Continued)

FOREIGN PATENT DOCUMENTS

| EP | 0653632 A1 | 5/1995 |
| EP | 1111703 A2 | 6/2001 |
| JP | 61-003054 A | 1/1986 |

OTHER PUBLICATIONS

Teterycz et al., Anomalous behaviour of new thick film gas sensitive composition, 1998, Elsevier Science S.A., Sensors and Actuators B 47, p. 153-157.*

(Continued)

*Primary Examiner* — Paul Hyun
*Assistant Examiner* — Robert Eom
(74) *Attorney, Agent, or Firm* — Benesch, Friedlander, Coplan, & Aronoff, LLC; Benjamen E. Kern; Kraig K. Anderson

(57) ABSTRACT

A hydrogen sensitive composite sensing material based on cerium oxide with or without additives to enhance sensitivity to hydrogen, reduce cross-sensitivities to interfering gases, or lower the operating temperature of the sensor, and a device incorporating these hydrogen sensitive composite materials including a support, electrodes applied to the support, and a coating of hydrogen sensitive composite material applied over the electroded surface. The sensor may have in integral heater. The sensor may have a tubular geometry with the heater being inserted within the tube. A gas sensor device may include a support, electrodes applied to the support, and a dual sensor element to cancel unwanted effects on baseline resistance such as those resulting from atmospheric temperature changes. The hydrogen sensitive composite material or other gas sensitive materials may be used in the dual element gas sensor device.

39 Claims, 18 Drawing Sheets

(51) Int. Cl.
*G01N 33/00* (2006.01)
*H01M 8/04* (2006.01)

(56) References Cited

U.S. PATENT DOCUMENTS

| | | | |
|---|---|---|---|
| 4,614,669 | A | 9/1986 | Yannopoulos |
| 4,730,479 | A | 3/1988 | Pyke et al. |
| 5,635,627 | A | 6/1997 | Bytyn |
| 6,109,095 | A * | 8/2000 | Addiego ............... 73/31.06 |
| 6,202,471 | B1 * | 3/2001 | Yadav et al. ........... 73/31.05 |
| 2007/0141443 | A1 * | 6/2007 | Brown ..................... 429/40 |

OTHER PUBLICATIONS

Kim et al., Sensitivity enhancement for CO gas detection using SnO2-CeO2-PdOx system, 2004 Elsevier B.V., Sensors and Actuators B 107, pp. 825-830.*

Trinchi et al., Investigation of sol-gel prepared CeO2-TiO2 thin films for oxygen gas sensing, 2003 Elsevier B.V., Sensors and Actuators B 95, pp. 145-150.*

Katsuki et al., H2 selective gas sensor based on SnO2, 1998 Elsevier Science S.A., Sensors and Actuators B 52, pp. 30-37.*

Zhang et al., Effect of transition metal oxides on densification and electrical properties of Si-containing Ce 0.8 Gd 0.2 O 2-δ ceramics, 2004, Elsevier B.V., Splod State Ionics, 168, pp. 187-195.*

Borchert et al., Nanostructures, Gd-doped ceria promoted by Pt or Pd: investigation of the electronic and surface structures and relations to chemical properties, 2005, ACS, J. Phys. Chem. B, 109, pp. 20077-20086.*

Lu et al., Micro-type powder-sputtered thin film gas sensors with long-term stability, Proceedings of the 2006 IEEE International Conference on Mechatronics and Automation, Jun. 25-28, 2006, China, pp. 2111-2115.*

A.-M. Azad et al., Hydrocarbon and sulfur sensors for SOFC systems, Phase I Final Report, DOE Contract No. DE-FC26-02NT41576, Nov. 2003, p. 1-32.*

Kim, I. J. et al., Sensitivity Enhancement for CO Gas Detection Using a SnO2-CeO2-PdOx System, Sensors and Actuators B, 2005, vol. 107, pp. 825-830, Elselvier B.V.

Written Opinion issued for PCT/US07/21928, Mar. 13, 2008.

International Search Report issued for PCT/US07/21928, Mar. 13, 2008.

European Search Opinion issued for European Patent Application No. 07852744, Apr. 23, 2012.

Supplementary European Search Report issued for European Patent Application No. 07852744, Apr. 23, 2012.

* cited by examiner

Step (1): Extrusion and Sintering of

Step (2): Deposition of Patterned

Step (3): Deposition of Sensor Material

HYDROGEN SENSITIVE COMPOSITE MATERIAL, HYDROGEN GAS SENSOR, AND SENSOR FOR DETECTING HYDROGEN AND OTHER GASES WITH IMPROVED BASELINE RESISTANCE

CROSS-REFERENCE TO RELATED APPLICATIONS

Not applicable

STATEMENT REGARDING FEDERALLY SPONSORED RESEARCH

Not applicable

REFERENCE TO MICROFICHE APPENDIX

Not applicable

As the hydrogen fuel infrastructure evolves, fuel cells will be used to provide power for cars and homes and distributed hydrogen production systems (i.e., hydrogen filling stations) will become commonplace. Safe implementation of hydrogen as our fuel of the future will be critical to commercial acceptance of fuel cell technology. Hydrogen safety sensors are critical components of prototype fuel cell systems being manufactured today and will continue to be important components of the fuel cell systems of tomorrow. Conventional hydrogen sensors used in industries including semiconductor manufacturing, chemicals manufacturing, and petroleum refining do not satisfy the cost and functionality requirements of fuel cell applications, with conventional sensors generally being deficient in sensitivity, low cross-sensitivity to other contaminants such as carbon monoxide, hydrocarbons, and volatile organic compounds, response and recovery times, long-term stability, or a combination of these.

Hydrogen sensors for fuel cell applications must achieve all of the critical performance requirements at a cost that can be tolerated by the targeted application. For chemical resistor type hydrogen sensors, critical performance requirements generally include the following:

- $H_2$ Detection Range: 1000 ppm to 1% (1% $H_2$ is 25% of the lower flammability limit of hydrogen)
- $H_2$ Sensitivity: >50% resistance change at 1% $H_2$ (in air)
- Wide ambient temperature range: −40 to 200° C.
- Response time ($t_{90}$): <30 seconds ($t_{90}$ is the time to reach 90% change in resistance in response to a change in $H_2$ concentration).
- Ambient humidity range: 0 to 100% RH
- Cross-sensitivity: None to CO, $CH_4$, $NH_3$, humidity, VOC's, or any other gas that might be present in air
- No need for recalibration (requires stable baseline resistance and sensitivity)
- Power requirements: less than 1 watt and preferably lower
- Packaging and electronics interfaced with low-cost electronic circuitry (e.g., 0-5 volt signals)

One object of this invention is to provide materials that are extremely sensitive to hydrogen. Another object of the invention is to provide a hydrogen sensor device including the above-described hydrogen sensitive material, and particularly a hydrogen sensor device that is sensitive to $H_2$ in air, provides quantifiable resistive responses within the desired range of 1000 ppm to 1 percent $H_2$, does not exhibit cross-sensitivities to interfering gases such as CO and $CH_4$, exhibits rapid response and recovery times, is capable of operating over a wide temperature range, exhibits stable performance over long time periods, has low power requirements, and is easy to manufacture at low cost. Another object of the invention is to provide a tubular sensor device useful for chemical resistor type gas sensor materials. The sensor device may include a heater configuration to minimize the sensitivity of the sensor to variation in relative humidity. The sensor device also may include a novel dual sensor to cancel unwanted effects on baseline resistance such as those resulting from atmospheric temperature changes.

One embodiment of the invention is a hydrogen sensitive composite material comprising a cerium oxide composition. The cerium oxide composition is selected from cerium oxide, zirconium doped ceria, gadolinium doped ceria, samarium doped ceria, lanthanum doped ceria, yttrium doped ceria, calcium doped ceria, strontium doped ceria, and mixtures thereof.

The hydrogen sensitive composite material also may comprise a modifier selected from tin oxide, indium oxide, titanium oxide, copper oxide, cobalt oxide, tungsten oxide, molybdenum oxide, nickel oxide, iron oxide, niobium oxide, vanadium oxide, a transition metal oxide, a mixture of transition metal oxides, a solid solution containing at least one transition metal oxide, a compound containing at least one transition metal oxide, and a mixture of at least two compounds each containing at least one transition metal oxide. In addition, the hydrogen sensitive composite material may comprise a noble metal promoter that may be selected from palladium, ruthenium, platinum, gold, rhodium, iridium, and a combination thereof. The hydrogen sensitive composite material also may comprise both a modifier and a promoter. The hydrogen sensitive composite material of claim 5 may comprise 1-100 wt % of a cerium oxide composition, 0-99 wt % of a modifier, and 0-99 wt % of a noble metal promoter.

Another embodiment of the invention is a hydrogen gas sensor device, comprising a support, electrodes applied to a surface of the support, and a sensor coating applied to the electroded surface of the support, with the sensor coating comprising the above=described hydrogen sensitive composite material. The support may be formed from a material selected from aluminum oxide, yttria stabilized zirconia, cerium oxide, gadolinium doped ceria, magnesium aluminate, and magnesium oxide.

The hydrogen gas sensor device also may comprise an integral resistive heater. The operating temperature may be selected to control the cross-sensitivity of the sensor device to gases other than hydrogen. The resistance of the heater may be selected to control the sensitivity of the sensor device to relative humidity. The support may be a micro-tubular support and the resistive heater may be inserted into the interior of the support and bonded at the tube ends. Alternatively, the support may be planar and the resistive heater may be applied to the support surface opposite the electroded surface.

Yet another embodiment of the invention is a gas sensor device comprising a support, electrodes applied to a surface of the support, and a dual sensor element in electrical communication with the electrodes. The dual sensor element comprises a first sensor including an unpromoted composite material relatively insensitive to the target gas, a second sensor including a promoted composite material sensitive to the target gas, and an apparatus for comparing a measurement obtained from the first sensor element and a measurement obtained from the second sensor element and using this comparison to compensate for the adverse effect of an environmental condition on the baseline resistance of the gas sensor device. The first and second sensor elements may be located on the same support. The support may be a micro-tubular support and a resistive heater may be inserted within the support and bonded at the tube ends. The operating temperature of the gas sensor device including a resistive heater may be selected to control the cross-sensitivity of the sensor device to gases other than the target gas. The resistance of the heater may be selected to control the sensitivity of the sensor device to relative humidity. The dual sensor element may be selected to compensate for the adverse effect of an environmental condition other than relative humidity on the baseline resistance of the gas sensor device. The gas sensitive composite material is a hydrogen sensitive composite material, more specifically, a cerium oxide composition.

BRIEF DESCRIPTION OF THE DRAWINGS

These and further objects of the invention will become apparent from the following detailed description.

DETAILED DESCRIPTION

Figure 1:
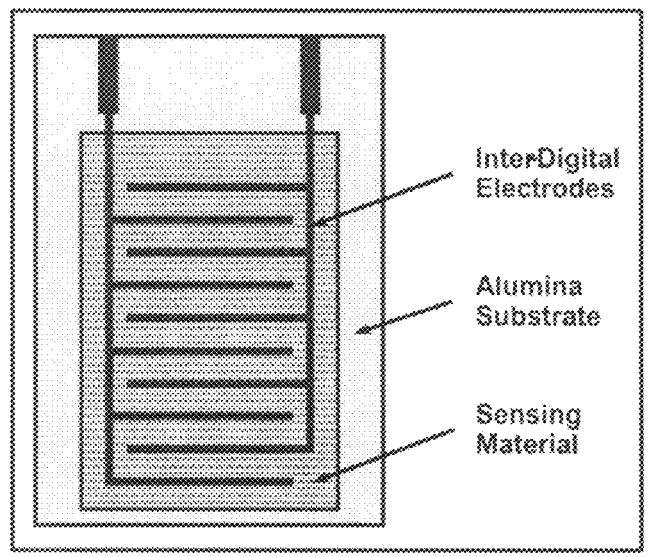
FIG. 1 is a schematic diagram of an inter-digital electrode (IDE) substrate used for planar sensor fabrication and testing.

The present invention provides hydrogen sensitive composite material based on cerium oxide. The hydrogen sensitivity is based on a large and reversible change in the electrical resistance of a cerium oxide thick film on a heated substrate or under operating conditions that avoid the need for a heated substrate. The cerium oxide composition may include additives to enhance sensitivity to hydrogen, reduce cross-sensitivities to interfering gases, and lower the operating temperature. The hydrogen sensitive composite material is capable of detecting hydrogen levels ranging from approximately 500 ppm up to and above 1% hydrogen in air. It exhibits fast response and recovery times to hydrogen and minimal cross sensitivity to interfering gases such as carbon monoxide and methane.

The hydrogen sensitive composite material may comprise a cerium oxide based composition including but not limited to cerium oxide, zirconium doped ceria, gadolinium doped ceria, samarium doped ceria, lanthanum doped ceria, yttrium doped ceria, calcium doped ceria, strontium doped ceria, and mixtures thereof. The precursor to the cerium oxide based composition may contain fugitive materials to increase the porosity of the composite material if desired. As used herein, the term "cerium oxide based composition" includes mixtures of a cerium oxide based composition with inert materials (e.g., aluminum oxide) provided that the amount of ceria is sufficient to achieve the desired response to the presence of hydrogen.

The hydrogen sensitive composite material also may comprise a second phase modifier, a noble metal promoter, or a combination of these. The modifier may comprise tin oxide, indium oxide, titanium oxide, copper oxide, cobalt oxide, tungsten oxide, molybdenum oxide, nickel oxide, iron oxide, niobium oxide, vanadium oxide, a transition metal oxide, a mixture of transition metal oxides, solid solutions containing one or more transition metal oxide, or one or more compounds each containing at least one transition metal oxide. The promoter may comprise palladium, ruthenium, platinum, gold, rhodium, iridium, or combinations of two or more noble metals. Compositions useful for detecting hydrogen extend over a broad range of formulations, such that the amount of the ceria containing phase may be from 1 to 100 weight percent, the amount of the modifier phase may be from 0 to 99 percent, and the amount of the precious metal promoter may be from 0 to 99 weight percent.

The hydrogen sensitive composite material of the present invention may be incorporated into a hydrogen sensor device for use in any residential or industrial application in which hydrogen may be present. These sensor devices are suitable for use in various applications including continuous area monitoring of dangerous levels of hydrogen in air. Such monitoring may take place inside the housing for a fuel cell stack, reformer, or development test stand, or in more open locations such as laboratories, refueling stations, or garages. Applications such as these in which the sensor device is used for long term monitoring require that the sensor device operate over a wide range of environmental conditions without producing false alarms, since even sensors used indoors in controlled environments are likely to encounter broad swings in temperature and humidity.

Two approaches generally are available to make a sensor that is immune to changes in environmental conditions such as temperature and humidity. First, compensation may be provided to adjust a signal from a sensor element affected by temperature or humidity based on external feedback. This may be accomplished, for example via programmed logic in the electronics into which the sensor is integrated. However, this approach is cumbersome, requires calibration of the environmental impact on the sensor signal, and may be subject to drift over the sensor life. The second preferred approach is to provide a sensor element having a signal that is not affected by changes in environmental conditions and therefore requires no compensation.

A hydrogen sensor device according to the present invention comprises a support, electrodes applied to a surface of the support, and a sensor coating of hydrogen sensitive material applied over the electroded support. The sensor device may have a tubular or a planar geometry.

The sensor device may have an integral resistive heater or may be used under conditions that avoid the need for an integral heater, for example, if the sensor material works at room temperature or the gas to be sensed is at an elevated temperature. If such a heater is used, the heater resistance is selected to minimize the sensitivity of the hydrogen sensitive material to variation in relative humidity. The operating temperature may be selected to control the cross-sensitivity of the sensor device to gases other than hydrogen. Furthermore, the resistance and resulting current of this heater may be selected to minimize unwanted sensitivity of the sensor to variation in relative humidity. The sensor device may also effectively detect certain other gases even when no heater is present if the sensor materials for that gas perform appropriately at the ambient temperature, the stream of gas to be analyzed is at an elevated temperature, or the sensor device will be used in a tube oven or similar environment.

The support may be made from aluminum oxide, yttria stabilized zirconia, cerium oxide, gadolinium doped ceria, magnesium aluminate, magnesium oxide, or any other ceramic material with sufficiently low electrical conductivity for sensor applications. Other support material compositions also are possible, depending on the gas sensing application, the sensor coating material, and the operating temperature. The support and the sensor coating may be formed from essentially the same material to eliminate thermal expansion mismatches but this is not required in all applications. For example, the support for the hydrogen sensor of the present invention may be made from aluminum oxide ($Al_2O_3$) or magnesium oxide (MgO), which would have advantages with respect to higher mechanical strength and thermal conductivity.

The electrodes applied to the support may be gold, silver, platinum, or any suitable metal. An inter-digital electrode pattern is described below but such a pattern is not essential to the successful operation of the micro-tubular sensor of the present invention. Any electrode geometry will work as long as the resistance of the sensor material coating is in the desired range within its operational temperature range.

One embodiment of the hydrogen sensor device may comprise a planar ceramic support, electrodes applied to a surface of the support, and a coating of the above-described hydrogen sensitive composite material applied to the electroded surface. A resistive heater may be printed on or bonded to the opposite side of the support, or contained within the support itself.

Another embodiment of the hydrogen sensor device may comprise a ceramic micro-tubular support, electrodes applied to the outer surface of the support, and a coating of the above-described hydrogen sensitive composite material applied onto the electroded outer surface of the support. The tubular support provides increased surface to volume ratio. The support tube may have an outer diameter of 0.5 to 5 mm and a wall thickness of 100-1000 microns. When a resistive heater is used, the heater wire (described further below) may be inserted into the interior of the ceramic micro-tube and bonded at the tube ends such that essentially all of the heat is applied to the tubular sensor when current is applied to the heater wire rather than lost to the environment, greatly reducing heating power requirements compared to a planar support.

The present invention also includes a gas sensor device with improved baseline resistance to the adverse effects of an environmental condition. The gas sensor device may comprise a support, electrodes applied to the support, and a dual sensor element. The dual sensor includes two different sensor coating materials that are selected to cancel unwanted environmental effects such as ambient temperature variation. Each of the sensors may be located on its own support (with separate heaters if needed) or both sensors may be located on a single support. A dual sensor element may be included in the above-described hydrogen sensor device.

Hydrogen-sensitive composite sensor materials useful in the present invention were developed and demonstrated using a prior art planar device platform shown in FIG. 1. The planar device has coatings of sensor materials deposited onto a ceramic substrate (aluminum oxide) with inter-digital electrodes (IDEs). Lead wires are attached to enable measurement of a resistance proportional to the electrical resistivity of the sensor material. The planar device may be placed in a tube furnace to determine the resistive responses of the sensor material coating to hydrogen or other gases of interest at different temperatures. Alternatively, a heater may be printed on or bonded to the opposite face of the planar device to heat the substrate to the desired operating temperature without a furnace.

Figure 12:
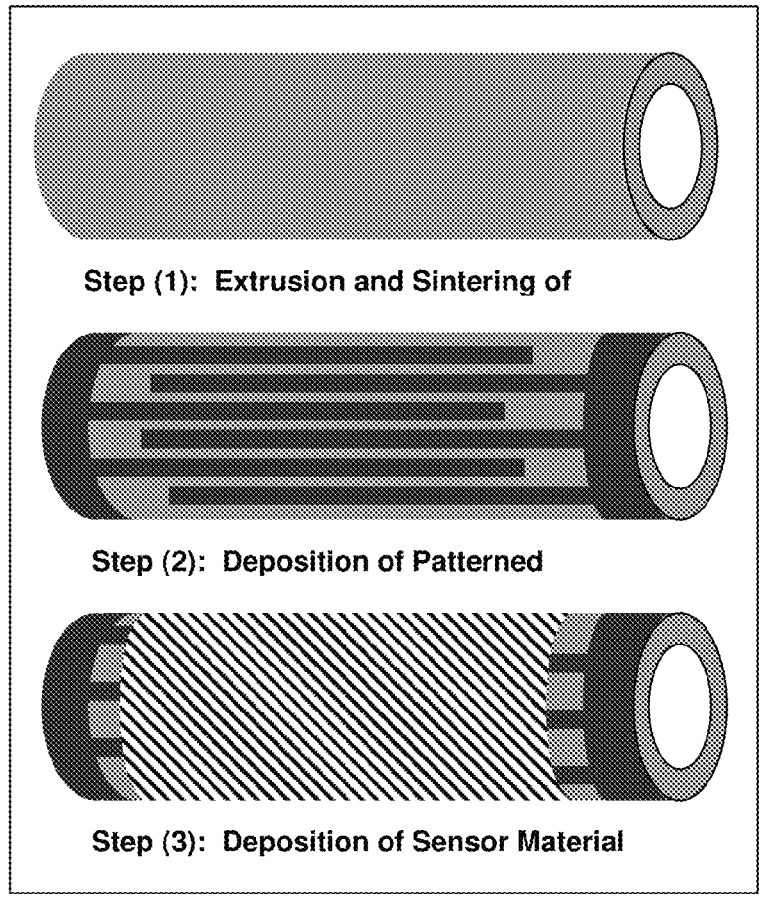
FIG. 12 is a schematic diagram showing the manufacturing steps used to produce the micro-tubular sensors of Example 20.
Figure 31:
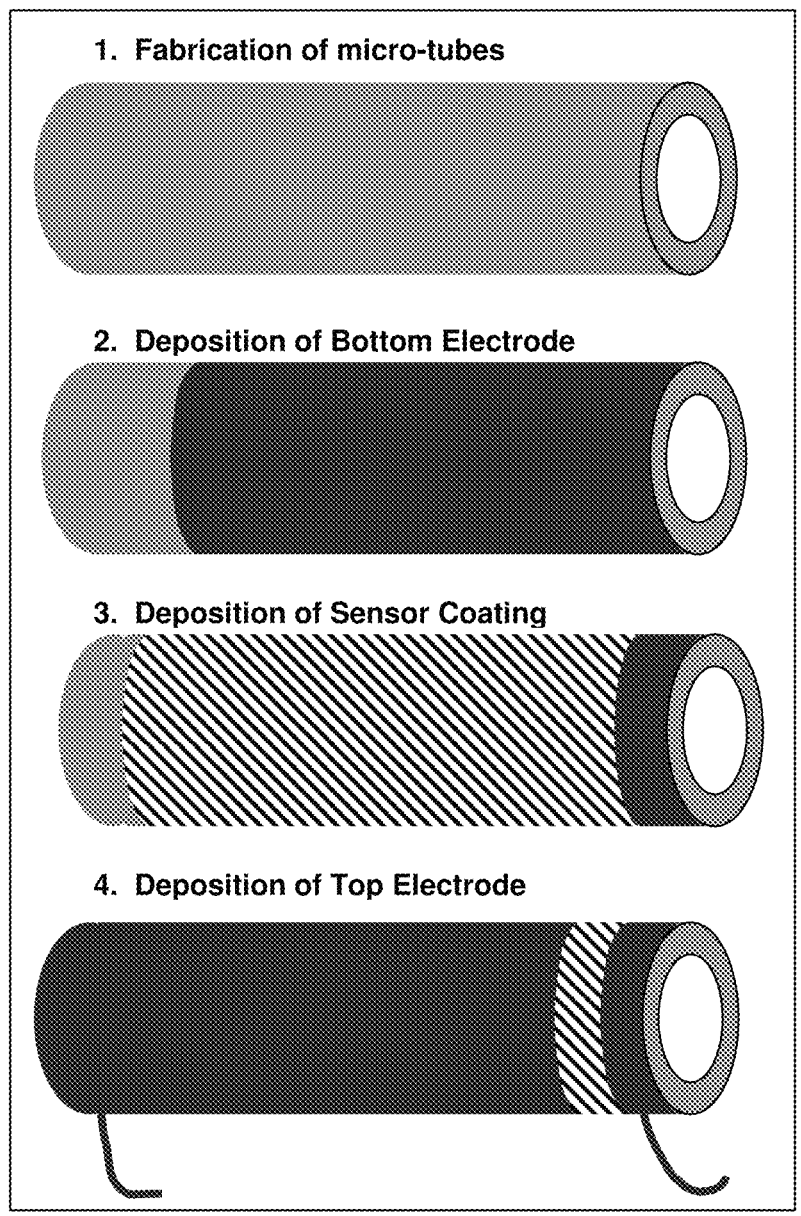
FIG. 31 is a schematic diagram showing the manufacturing steps used to produce another embodiment of micro-tubular sensors according to the present invention.
Figure 32:
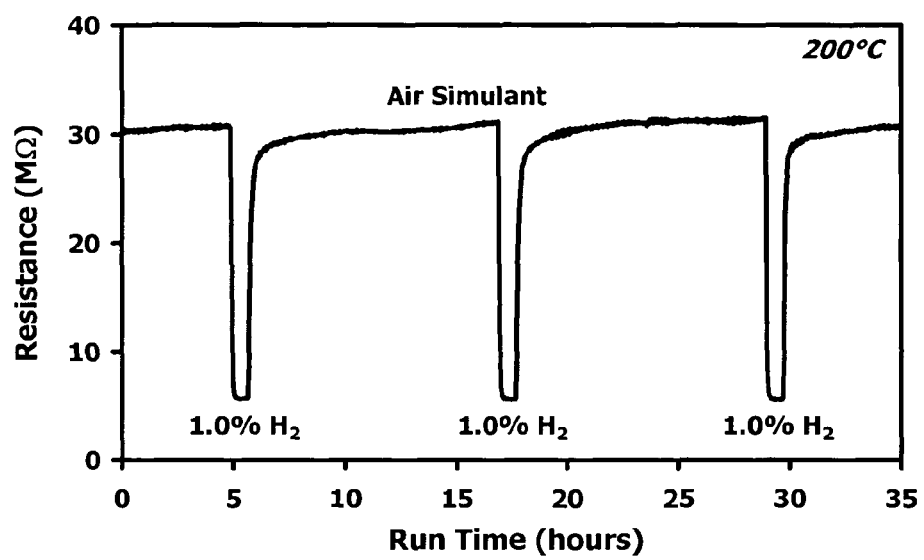
FIG. 32 is a graph showing the sensitivity of a micro-tubular hydrogen sensor prepared using the manufacturing steps shown in FIG. 31, according to the present invention.

Electrodes were applied to the outer surface of the tubular support and a coating of a sensor material was applied over the electroded surface. The sensor device may be prepared as shown in FIG. 12 by applying electrodes in a pattern to the outer surface of the tubular support and then applying a coating of a sensor material over the electroded surface. Alternatively, the sensor may be produced as shown in FIG. 31 by applying an electrode material to a portion of the tubular support adjacent to a first end of the support but not covering the portion adjacent to the second end of the support; applying a coating of a sensor material offset from the electrode layer such that a portion of the electrode layer nearest the first end remains exposed and the remainder of the electrode layer and a portion of the uncovered tubular support adjacent to the second end are covered by the sensor material coating; and applying a second layer of an electrode material offset from the sensor material coating such that a portion of the sensor material coating nearest the first end remains exposed and the remainder of the sensor material coating and the uncoated portion of the tubular support are covered by the second electrode layer. Data obtained on a device fabricated in this fashion are shown in FIG. 32.

Sensor devices were tested using a digital multimeter connected via serial port to a computer for controlled data acquisition. The sensor test stands had fully automated data collection and process control through integration with LabVIEW™ software. A programmable tube furnace, housed in a leak-tight quartz tube with wire feedthroughs for electrical measurements, was used to control the temperature of the sensor.

The simulated gas mixtures were produced from three standard compressed gas cylinders: one that contained 2% $H_2$ in nitrogen, a second that contained pure nitrogen, and a third that contained a mixture of oxygen and nitrogen. Digital mass flow controllers were used to control the gas composition within the sensor chamber.

The following examples describe the development of hydrogen sensitive material formulations based on cerium oxide.

EXAMPLE 1

$H_2$ Sensors Based Solely on Cerium Oxide

Figure 2:
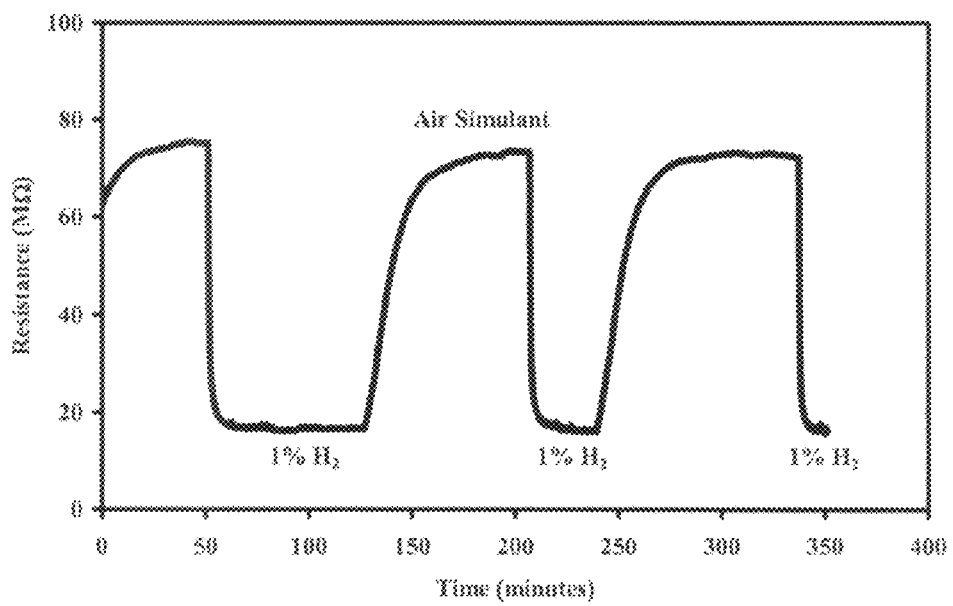
FIG. 2 is a graph of the hydrogen sensitivity of the $CeO_2$ based sensor of Example 1, showing repeatable responses to 1% $H_2$ at 400° C.
Figure 3:
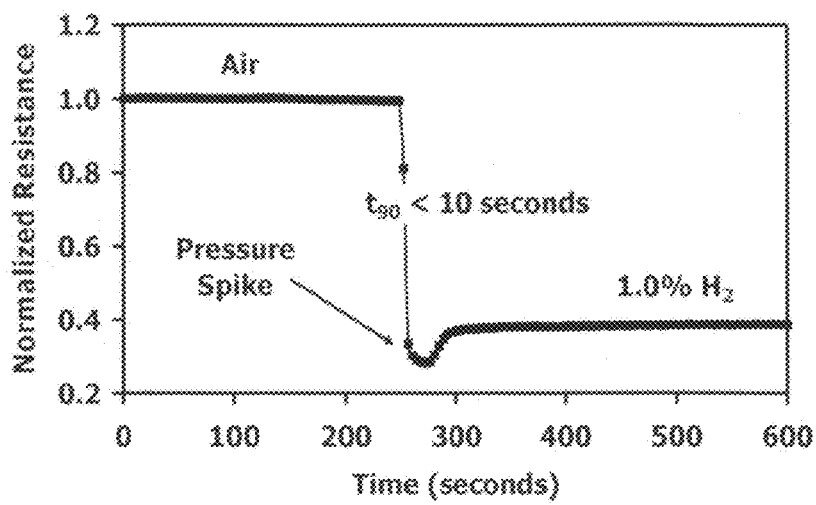
FIG. 3 is a graph of the response of the $CeO_2$ based sensor of Example 1 to 1% $H_2$ in air at 400° C.

An ink was prepared by mixing 14 $m^2/g$ surface area $CeO_2$ powder with Johnson Matthey 63/2 Medium vehicle in a 2:1 ratio of powder to vehicle using a mortar and pestle. The ink was painted on the surface of 5-mm×5-mm aluminum oxide substrate with inter-digital electrodes and then annealed at 800° C. for one hour. The sensor was tested as described above at various temperatures. Maximum hydrogen sensitivity was obtained at a temperature of 400° C. As shown in FIG. 2, the planar device with a sensor coating material based solely on $CeO_2$ provides a large and repeatable response to 1% hydrogen. When 1% $H_2$ is introduced, the device resistance is reduced from about 75 MΩ to about 18 MΩ, which corresponds to a sensitivity of about 75 percent. When $H_2$ is removed, the device resistance returns to its original level. As shown in FIG. 3, the response of this sensor to hydrogen is extremely rapid, taking less than about ten seconds to achieve 90% of its resistance change after 1% $H_2$ is introduced. While a sensor material bases solely on $CeO_2$ exhibited very high sensitivity to hydrogen, a high operating temperature was required to achieve maximum sensitivity, probably because resistance was extremely high at lower temperatures. Operation of the sensor at such high temperatures would require relatively high heater power for the sensor.

EXAMPLE 2

$H_2$ Sensors Based on Gadolinium Doped Ceria

Figure 4:
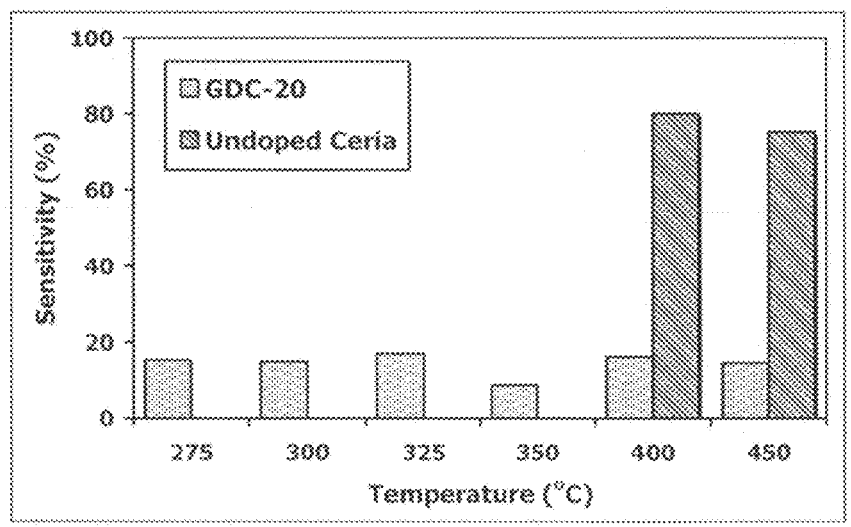
FIG. 4 is a graph of hydrogen sensitivity versus temperature for the $CeO_2$ and GDC sensors of Examples 1 and 2, respectively.

To reduce the operating temperature, 20 mol % of gadolinium was substituted in the crystal structure of $CeO_2$, creating oxygen vacancies in the structure and increasing ionic conductivity at lower temperatures. This ceria based electrolyte composition (GDC) is well known in the field of solid state ionics, although the sensitivity of the composition to hydrogen levels present in fuel cell applications was not known. The GDC sensor was made as described in Example 1. An ink was prepared by mixing 12 $m^2/g$ surface area GDC powder with Johnson Matthey 63/2 Medium vehicle in a 2:1 ratio of powder to vehicle using a mortar and pestle. The ink was painted on the surface of 5-mm×5-mm aluminum oxide substrate with inter-digital electrodes and then annealed at 800° C. for one hour. The sensor was tested as described above at various temperatures. Hydrogen sensitivity was obtained over a wide range of temperature. The data in FIG. 4, which compare the hydrogen sensitivities (percent change of resistance after exposure to 1% $H_2$) of the $CeO_2$ sensor of Example 1 with the GDC sensor of Example 2, demonstrate that the GDC sensor retains sensitivity to hydrogen at temperatures as low as 275° C. However, the magnitude of hydrogen sensitivity was much lower for the GDC sensor than for the $CeO_2$ sensor.

EXAMPLES 3, 4, 5, AND 6

$CeO_2$ Based Sensors with Second Phase Additions of $SnO_2$ or $In_2O_3$

The effects of second phase additions of $In_2O_3$ or $SnO_2$ on hydrogen sensitivity of $CeO_2$ based sensors were evaluated. Multiple composite inks were prepared using methods described above for Examples 1 and 2. High surface area $SnO_2$ and $In_2O_3$ powders were added to $CeO_2$ powder at 2.5 and 5 wt % levels. Planar sensors were fabricated and tested, also using previously described methods. Hydrogen sensitivities were measured at different temperatures, with data presented in Table 1.

TABLE 1

Sensitivities of $CeO_2$ based sensors to 1% $H_2$ in dry simulated air at different temperatures.

| Ex. | Formulation | 400° C. | 415° C. | 425° C. | 430° C. | 450° C. | 500° C. | 550° C. | 575° C. | 600° C. |
|---|---|---|---|---|---|---|---|---|---|---|
| 1 | $CeO_2$ | 80.0% | | | | 75.3% | | | | |
| 3 | $CeO_2$ (2.5 wt % $SnO_2$) | | | | 72.5% | 72.9% | 61.1% | 49.0% | | 41.8% |
| 4 | $CeO_2$ (5.0 wt % $SnO_2$) | | 76.1% | | | 67.6% | 58.1% | 32.3% | | 22.0% |
| 5 | $CeO_2$ (2.5 wt % $In_2O_3$) | | | 51.2% | | 48.5% | 32.2% | 24.2% | | 28.0% |
| 6 | $CeO_2$ (5.0 wt % $In_2O_3$) | | | 46.3% | | 51.4% | 38.9% | 36.4% | | 28.7% |

The interference resistance, or cross-sensitivity, for each sensor was also evaluated by testing the response of the sensors to 200 ppm CO and to 0.5 vol % $CH_4$. The 200 ppm CO level was selected because this is considered the evacuation level for industrial facilities. The 0.5 vol % $CH_4$ level was selected because this corresponds to 10% of the lower explosive limit of methane. Comparisons were made by determining the "relative sensitivity" to hydrogen using the following equation:

Relative Sensitivity=(Sensitivity to 1% $H_2$)−(Cross-sensitivity)

If a sensor has no cross-sensitivity to CO, the relative sensitivity equals the sensitivity for that sensor. A negative relative sensitivity means that the sensor is more sensitive to the interference gas than it is to hydrogen. The relative sensitivities for $CeO_2$ based sensors are provided in Tables 2 and 3.

TABLE 2

Relative sensitivities of $CeO_2$ based sensors to 1% $H_2$ in simulated air at different temperatures in the presence of 200 ppm of carbon monoxide.

| Ex. | Formulation | 400° C. | 415° C. | 425° C. | 430° C. | 450° C. | 500° C. | 550° C. | 575° C. | 600° C. |
|---|---|---|---|---|---|---|---|---|---|---|
| 1 | $CeO_2$ | 59.6% | | | | | | | | |
| 3 | $CeO_2$ (2.5 wt % $SnO_2$) | | | | 36.0% | 49.1% | 51.4% | 43.2% | 39.7% | |
| 4 | $CeO_2$ (5.0 wt % $SnO_2$) | | 36.2% | | | 47.3% | 46.9% | 25.0% | | 17.8% |
| 5 | $CeO_2$ (2.5 wt % $In_2O_3$) | | | 25.8% | | 31.4% | 23.6% | 15.3% | | 27.5% |
| 6 | $CeO_2$ (5.0 wt % $In_2O_3$) | | | 22.3% | | 36.8% | 32.4% | 34.5% | | 27.5% |

TABLE 3

Relative sensitivities of $CeO_2$ based sensors to 1% $H_2$ in simulated air at different temperatures in the presence of 0.5 vol % of methane.

| Ex. | Formulation | 400° C. | 415° C. | 425° C. | 430° C. | 450° C. | 500° C. | 550° C. | 575° C. | 600° C. |
|---|---|---|---|---|---|---|---|---|---|---|
| 1 | $CeO_2$ | | | | | | | | | |
| 3 | $CeO_2$ (2.5 wt % $SnO_2$) | | | | 51.1% | 53.9% | 51.5% | 39.2% | 35.7% | |
| 4 | $CeO_2$ (5.0 wt % $SnO_2$) | | 62.8% | | | 49.9% | 12.3% | −6.9% | | −6.5% |
| 5 | $CeO_2$ (2.5 wt % $In_2O_3$) | | | 15.6% | | 21.0% | 20.0% | 15.9% | | 20.7% |
| 6 | $CeO_2$ (5.0 wt % $In_2O_3$) | | | 24.0% | | 30.9% | 20.6% | 2.00% | | 1.80% |

EXAMPLES 7, 8, 9, AND 10

GDC Based Sensors with Second Phase Additions of $SnO_2$ or $In_2O_3$

The effects of second phase additions of $In_2O_3$ or $SnO_2$ on hydrogen sensitivity of GDC based sensors also were evaluated. Multiple composite inks were prepared using methods described above. High surface area $SnO_2$ and $In_2O_3$ powders were added to GDC powder at 2.5 and 5 wt % levels. Planar sensors were fabricated and tested, also using previously described methods. Hydrogen sensitivities and relative sensitivities were measured at different temperatures, with data presented in Tables 4 and 5, respectively.

TABLE 4

Sensitivities of GDC based sensors to 1% $H_2$ in dry simulated air at different temperatures.

| Ex. | Formulation | 225° C. | 230° C. | 250° C. | 275° C. | 300° C. | 325° C. | 350° C. | 400° C. | 450° C. |
|---|---|---|---|---|---|---|---|---|---|---|
| 1 | GDC | | 21.1% | | 15.2% | 14.8% | 17.0% | 8.70% | 16.2% | 14.4% |
| 7 | GDC (2.5 wt % $SnO_2$) | 20.8% | | 7.92% | | 12.5% | | 8.80% | | 27.9% |
| 8 | GDC (5.0 wt % $SnO_2$) | | | 14.0% | | 7.20% | | 23.5% | 8.35% | |
| 9 | GDC (2.5 wt % $In_2O_3$) | 16.8% | | 7.49% | | 19.4% | | 6.23% | | |
| 10 | GDC (5.0 wt % $In_2O_3$) | | | 4.86% | | 7.63% | | 21.4% | 6.30% | 7.32% |

TABLE 5

Relative Sensitivities of GDC based sensors to 1% $H_2$ in simulated air at different temperatures in the presence of carbon monoxide and methane.

| | | 200 ppm CO | | | | 0.5 vol % $CH_4$ | | | |
|---|---|---|---|---|---|---|---|---|---|
| Ex. | Formulation | 250° C. | 300° C. | 350° C. | 400° C. | 250° C. | 300° C. | 350° C. | 400° C. |
| 1 | GDC | | | | | | | | |
| 7 | GDC (2.5 wt % $SnO_2$) | 7.00% | 11.3% | | 30.5% | 7.30% | 12.0% | | 31.0% |
| 8 | GDC (5.0 wt % $SnO_2$) | 7.10% | 4.40% | 15.3% | 7.60% | 10.6% | 4.60% | 22.0% | 7.93% |
| 9 | GDC (2.5 wt % $In_2O_3$) | 10.6% | 16.9% | 6.6% | | 11.8% | 21.2% | 9.20% | |
| 10 | GDC (5.0 wt % $In_2O_3$) | | 5.43% | 14.8% | 6.80% | 11.2% | 12.7% | 23.2% | 8.70% |

Figure 5:
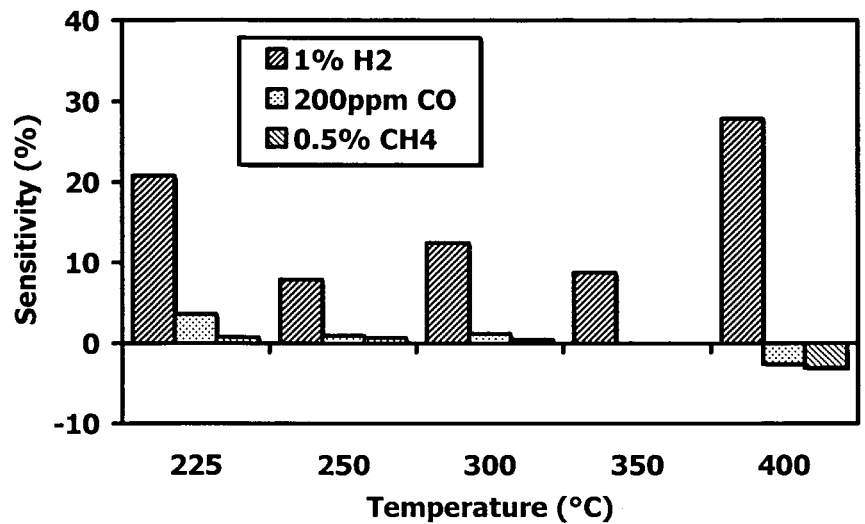
FIG. 5 is a graph of the resistive responses of the GDC (2.5% $SnO_2$) sensor of Example 7 to hydrogen, carbon monoxide, and methane at various temperatures, showing zero cross-sensitivity at 350° C.

During the above described testing, it was discovered that the operating temperature of the sensor could be used to tune-out the cross-sensitivities to CO and $CH_4$. For several samples, it was noted that cross-sensitivity to both CO and $CH_4$ changed from an n-type response (decreased resistance) to a p-type response (increased resistance) at a certain temperature. This phenomenon makes it possible to engineer sensors to be immune to interference gases. The GDC (2.5% $SnO_2$) sensor of Example 7 showed no response to either CO or $CH_4$ at 350° C., as shown in FIG. 5.

EXAMPLES 11, 12, 13 AND 14

Composite $CeO_2$ Sensors with Pd and Ru Promoters $CeO_2$ based composite sensor formulations with 5-wt % second phase additions of $SnO_2$ or $In_2O_3$ were subjected to studies aimed at optimizing sensitivity through additions of a noble metal promoter. Ruthenium and palladium each was evaluated at 1-wt % levels. Palladium (II) 2,4-pentanedionate and ruthenium (III) 2,4-pentanedionate were dissolved in the Johnson Matthey vehicle and the sensor inks were prepared using the same procedure as previously described. Planar sensors were fabricated and tested at different temperatures, also using previously described methods. Hydrogen sensitivity data for these $CeO_2$ based sensors are presented in Table 6 and relative sensitivity data are presented in Tables 7 and 8. Palladium additions increased sensitivity to hydrogen for the $CeO_2$ based sensors. However, palladium additions increased cross-sensitivities to CO and $CH_4$ for $CeO_2$ (5% $SnO_2$) sensors, which led to lower relative sensitivities. Palladium had a slightly positive effect on the relative sensitivities of the $CeO_2$ (5% $In_2O_3$) sensors. Ruthenium additions had little effect on hydrogen sensitivity and relative sensitivities of the $CeO_2$ based sensors.

TABLE 6

Sensitivities of palladium and ruthenium promoted $CeO_2$ based sensors to 1% $H_2$ in simulated air at different temperatures.

| Ex. Formulation | Promoter | 450° C. | 475° C. | 500° C. | 550° C. | 600° C. | 650° C. |
|---|---|---|---|---|---|---|---|
| 4 $CeO_2$ (5.0 wt % $SnO_2$) | none | 67.6% | | 58.1% | 32.3% | 22.0% | |
| 11 $CeO_2$ (5.0 wt % $SnO_2$) | 1 wt % Pd | 95.0% | | 92.3% | 88.1% | 67.4% | |
| 12 $CeO_2$ (5.0 wt % $SnO_2$) | 1 wt % Ru | 80.3% | | 72.8% | 51.7% | 31.9% | |
| 6 $CeO_2$ (5.0 wt % $In_2O_3$) | none | 51.4% | | 38.9% | 36.4% | 28.7% | |
| 13 $CeO_2$ (5.0 wt % $In_2O_3$) | 1 wt % Pd | | 93.8% | 94.7% | 91.7% | 70.8% | 26.8% |
| 14 $CeO_2$ (5.0 wt % $In_2O_3$) | 1 wt % Ru | 65.2% | | 59.6% | 45.7% | 25.2% | 17.2% |

TABLE 7

Relative sensitivities of Pd and Ru promoted $CeO_2$ based sensors to 1% $H_2$ in simulated air at different temperatures in the presence of 200 ppm of carbon monoxide.

| Ex. Formulation | Promoter | 450° C. | 475° C. | 500° C. | 550° C. | 600° C. | 650° C. |
|---|---|---|---|---|---|---|---|
| 4 $CeO_2$ (5.0 wt % $SnO_2$) | none | 47.3% | | 46.9% | 25.0% | 17.8% | |
| 11 $CeO_2$ (5.0 wt % $SnO_2$) | 1 wt % Pd | 30.5% | | 26.9% | 42.2% | 45.6% | |
| 12 $CeO_2$ (5.0 wt % $SnO_2$) | 1 wt % Ru | 48.3% | | 54.3% | 43.8% | 28.6% | |
| 6 $CeO_2$ (5.0 wt % $In_2O_3$) | none | 36.8% | | 32.4% | 34.5% | 27.5% | |
| 13 $CeO_2$ (5.0 wt % $In_2O_3$) | 1 wt % Pd | | 41.8% | 44.5% | 40.0% | 41.3% | 17.6% |
| 14 $CeO_2$ (5.0 wt % $In_2O_3$) | 1 wt % Ru | 47.4% | | 46.7% | 42.3% | 23.3% | 16.8% |

TABLE 8

Relative sensitivities of Pd and Ru promoted $CeO_2$ based sensors to 1% $H_2$ in simulated air at different temperatures in the presence of 0.5 vol % of methane.

| Ex. Formulation | Promoter | 450° C. | 475° C. | 500° C. | 550° C. | 600° C. | 650° C. |
|---|---|---|---|---|---|---|---|
| 4 $CeO_2$ (5.0 wt % $SnO_2$) | none | 49.9% | | 12.3% | −6.90% | −6.50% | |
| 11 $CeO_2$ (5.0 wt % $SnO_2$) | 1 wt % Pd | 42.7% | | 42.3% | 39.5% | 5.10% | |
| 12 $CeO_2$ (5.0 wt % $SnO_2$) | 1 wt % Ru | 47.8% | | 49.8% | 16.3% | −9.30% | |
| 6 $CeO_2$ (5.0 wt % $In_2O_3$) | none | 30.9% | | 20.6% | 2.00% | 1.80% | |
| 13 $CeO_2$ (5.0 wt % $In_2O_3$) | 1 wt % Pd | | 32.7% | 19.8% | 23.6% | 1.80% | 30.1% |
| 14 $CeO_2$ (5.0 wt % $In_2O_3$) | 1 wt % Ru | 25.1% | | 32.3% | 8.80% | −8.30% | −5.00% |

EXAMPLES 15, 16, 17 AND 18

Composite GDC Sensors with Pd and Ru Promoters

GDC based composite sensor formulations with 5-wt % second phase additions of $SnO_2$ or $In_2O_3$ were studied to optimize sensitivity through additions of a noble metal promoter. Ruthenium and palladium each was evaluated at 1-wt % levels. Palladium (II) 2,4-pentanedionate and ruthenium (III) 2,4-pentanedionate were dissolved in the Johnson Matthey vehicle and the sensor inks were prepared using the same procedures as previously described. Planar sensors were fabricated and tested at different temperatures, also using previously described methods. Hydrogen sensitivity data for these GDC based sensors are presented in Table 9 and relative sensitivity data are presented in Tables 10 and 11.

TABLE 9

Sensitivities of palladium and ruthenium promoted GDC based sensors to 1% H$_2$ in simulated air at different temperatures.

| Ex. | Formulation | Promoter | 250° C. | 275° C. | 300° C. | 350° C. | 400° C. | 450° C. |
|---|---|---|---|---|---|---|---|---|
| 8  | GDC (5.0 wt % SnO$_2$)   | None      | 14.0% |       | 7.20% | 23.5% | 8.40% |       |
| 15 | GDC (5.0 wt % SnO$_2$)   | 1 wt % Pd | 45.6% |       | 50.7% | 44.6% | 24.3% | 24.2% |
| 16 | GDC (5.0 wt % SnO$_2$)   | 1 wt % Ru | 19.8% |       | 19.1% | 11.8% | 20.1% |       |
| 10 | GDC (5.0 wt % In$_2$O$_3$) | None    | 4.86% |       | 7.63% | 21.4% | 6.30% | 7.32% |
| 17 | GDC (5.0 wt % In$_2$O$_3$) | 1 wt % Pd |     | 40.3% | 42.3% | 32.8% | 28.0% | 26.5% |
| 18 | GDC (5.0 wt % In$_2$O$_3$) | 1 wt % Ru |     | 19.3% | 17.0% | 12.0% | 20.8% |       |

TABLE 10

Relative sensitivities of Pd and Ru promoted GDC based sensors to 1% H$_2$ in simulated air at different temperatures in the presence of 200 ppm of carbon monoxide.

| Ex. | Formulation | Promoter | 250° C. | 275° C. | 300° C. | 350° C. | 400° C. | 450° C. |
|---|---|---|---|---|---|---|---|---|
| 8  | GDC (5.0 wt % SnO$_2$)   | None      | 7.10% |       | 4.40% | 15.3% | 7.60% |       |
| 15 | GDC (5.0 wt % SnO$_2$)   | 1 wt % Pd | 43.3% |       | 46.2% | 42.0% | 25.8% | 26.2% |
| 16 | GDC (5.0 wt % SnO$_2$)   | 1 wt % Ru | 13.8% |       | 16.8% | 11.5% | 18.7% |       |
| 10 | GDC (5.0 wt % In$_2$O$_3$) | None    |       |       | 5.43% | 14.8% | 6.80% | 6.69% |
| 17 | GDC (5.0 wt % In$_2$O$_3$) | 1 wt % Pd |     | 42.8% | 44.2% | 34.6% | 30.1% | 29.6% |
| 18 | GDC (5.0 wt % In$_2$O$_3$) | 1 wt % Ru |     | 22.1% | 18.3% | 13.6% | 20.4% |       |

TABLE 11

Relative sensitivities of Pd and Ru promoted GDC based sensors to 1% H$_2$ in simulated air at different temperatures in the presence of 0.5 vol % of methane.

| Ex. | Formulation | Promoter | 250° C. | 275° C. | 300° C. | 350° C. | 400° C. | 450° C. |
|---|---|---|---|---|---|---|---|---|
| 8  | GDC (5.0 wt % SnO$_2$)   | none      | 10.6% |       | 4.60% | 22.0% | 7.93% |       |
| 15 | GDC (5.0 wt % SnO$_2$)   | 1 wt % Pd | 43.4% |       | 46.3% | 41.4% | 25.2% | 26.7% |
| 16 | GDC (5.0 wt % SnO$_2$)   | 1 wt % Ru | 15.7% |       | 11.3% | 12.9% | 20.5% |       |
| 10 | GDC (5.0 wt % In$_2$O$_3$) | none    | 11.2% |       | 12.7% | 23.2% | 8.70% | 8.70% |
| 17 | GDC (5.0 wt % In$_2$O$_3$) | 1 wt % Pd |     | 42.5% | 44.4% | 32.8% | 30.1% | 28.8% |
| 18 | GDC (5.0 wt % In$_2$O$_3$) | 1 wt % Ru |     | 21.2% | 17.8% | 12.8% | 22.0% |       |

Figure 6:
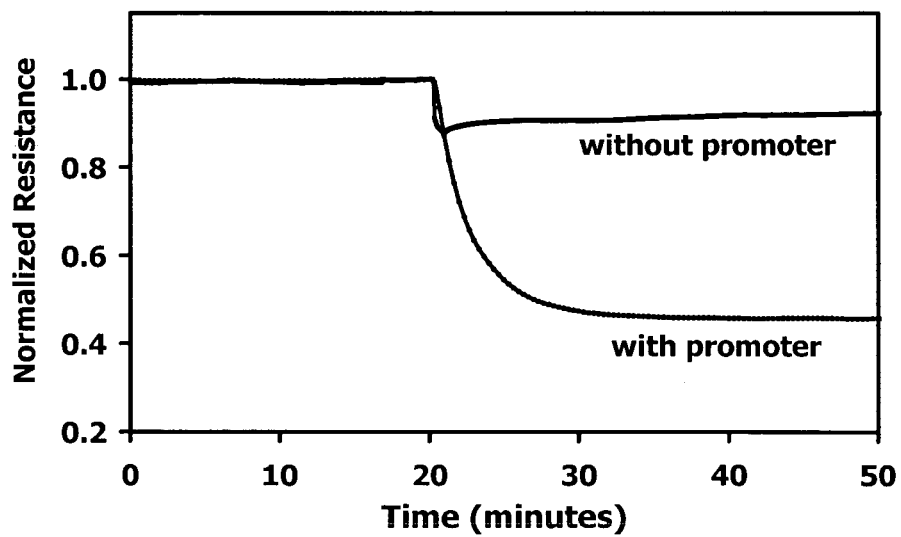
FIG. 6 is a graph of the effect of 1% palladium addition on hydrogen sensitivity of the GDC (5% $SnO_2$) sensors of Examples 8 and 15 at 250° C.
Figure 7:
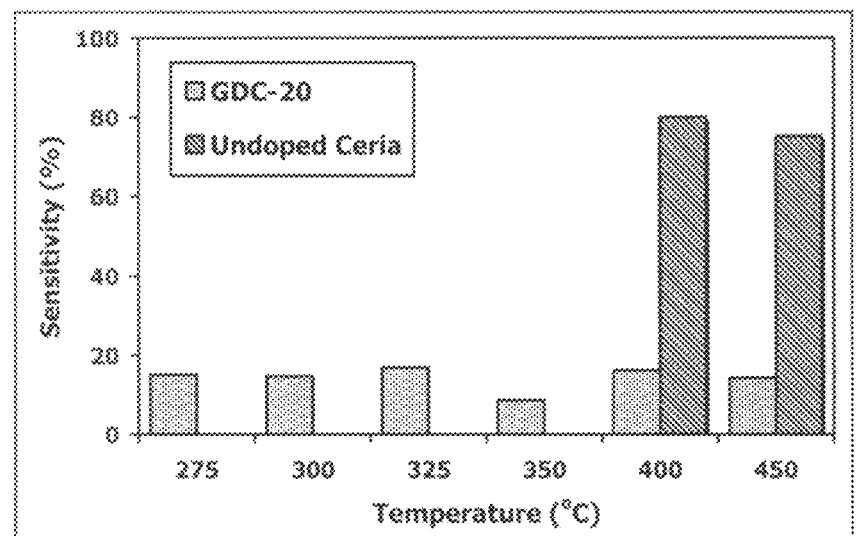
FIG. 7 is a graph of the effect of 1 wt % palladium addition on hydrogen sensitivity of GDC (5% $SnO_2$) sensors of Examples 8 and 15 at temperatures between 250 and 500° C.

For GDC based sensors, the presence of a palladium or ruthenium promoter increased hydrogen sensitivity. The largest improvement was observed for palladium additions, as shown in FIG. 6 for the Pd-doped GDC (5% SnO$_2$) sensor of Example 15. The Pd addition to GDC (5% SnO$_2$) sensors enhanced sensitivity to 1% H$_2$ by about a factor of four; this enhancement was observed over a wide range of operating temperatures (see FIG. 7). Based on the above described results, the 94% GDC/5% SnO$_2$/1% Pd sensor formulation of Example 15 was selected for work aimed at demonstrating prototype sensor elements.

Work to demonstrate prototype sensor elements focused on two types of sensor elements. The first type used the planar alumina substrate (described above) with the coating material deposited on the inter-digital electrodes and a resistive heater applied to the back side of the substrate. The second type used a novel tubular substrate in which electrodes and the sensor coatings were applied to the outside surface of a ceramic micro-tube and a resistive wire heater was inserted into the inside of the tube.

As described below in Example 19, performance of the planar device was limited by the inefficiency of the internal heater; the heater effectively provided a controlled temperature for the planar device but also lost heat to its surroundings. The structural bonding of the heater to the planar element, which is achieved in the "hot zone," also might result in performance limitations related to long-term degradation of the bond. The planar device also has a potential limitation related to differences in the thermal expansion coefficients of the aluminum oxide substrate (~8 ppm/° C.) and the ceria-based sensor coating (~13 ppm/° C.) that could result in failures during start-up and shut-down.

The novel tubular sensor device, described more fully in Example 20, overcomes these limitations, as noted below:

- The support component for the sensor is a porous ceramic tube with essentially the same composition (95% GDC/ 5% SnO$_2$) as the sensor coating material (94% GDC/5% SnO$_2$/1% Pd). Pd was omitted from the support material to minimize cost.
- The heat for the tubular sensor is provided by a wire heater located in the interior of the tube. Essentially all of the heat provided by the heater goes to heating the element and very little heat is lost to the surrounding environment.
- The bonding of the heater wire to the tubular sensor element occurs at the tube ends, which are at a lower temperature than the sensor element. This is a non-structural bond and should be less prone to failures caused by thermal expansion mismatch.
- The micro-tubular element offers a high surface to volume ratio, which leads to improved sensitivity compared to planar devices. As will be shown, this improved sensitivity results in lower operating temperature (and thus better long-term stability of baseline resistance and H$_2$ sensitivity.)

As will be shown, the resistance of the heater in the micro-tubular element can be selected to minimize the sensitivity of the sensor device to variation in relative humidity.

Although thermal expansion match is higher, other support tubes materials such as aluminum oxide and YSZ can be used, offering advantages such as cost, strength, and insulating properties.

The following examples illustrate the advantages of the tubular sensor structure:

EXAMPLE 19

Planar Hydrogen Sensor Element

Figure 8:
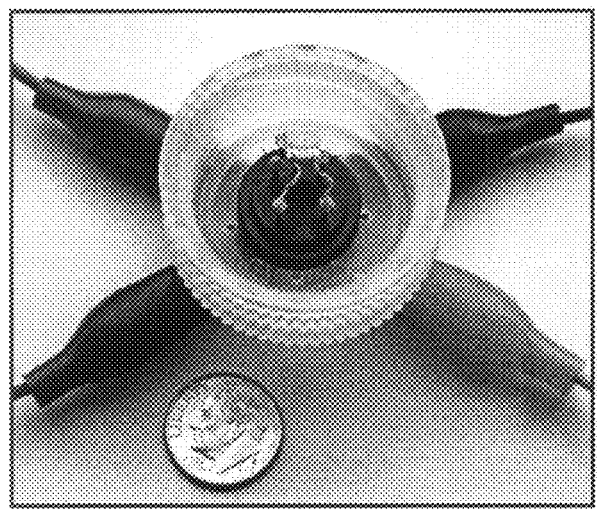
FIG. 8 is an image of an exemplary assembled prototype planar hydrogen sensor as described in Example 19.
Figure 9:
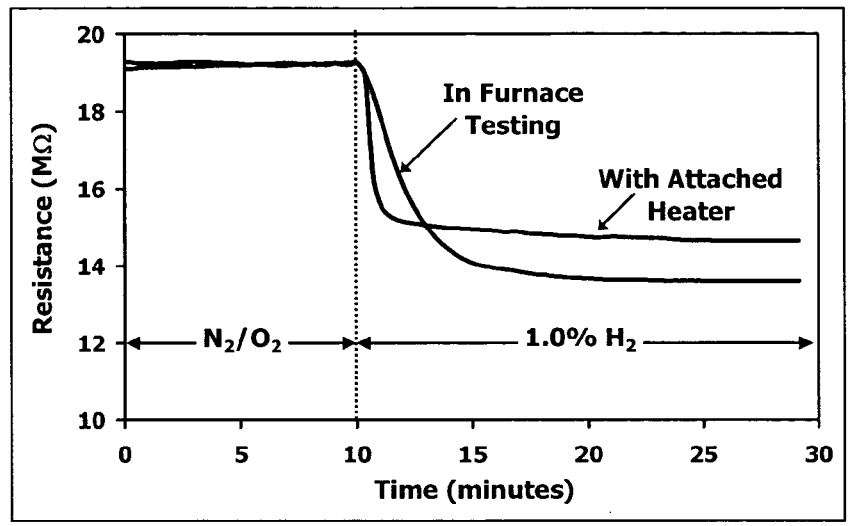
FIG. 9 is a graph of the hydrogen sensing performance of the planar prototype hydrogen sensor of Example 19.

A coating of the selected sensor material (94% GDC/5% $SnO_2$/1% Pd) was deposited onto an IDE substrate (5-mm square) and annealed at 800° C. for one hour. An 8.1Ω resistive heater was fabricated from a 34 AWG nickel-chromium 60 resistive heating wire. This heater was bonded to the back side of the IDE substrate using ceramic cement (Ceramabond 552-VFG high temperature ceramic adhesive). The planar sensor element is shown in FIG. 8. The performance of the sensor element (baseline resistance and $H_2$ sensitivity) was first tested in a tube furnace at 300° C. (the optimum operating temperature based on previously described results) with externally supplied heat (with the attached heater not energized). The sample was then removed from the tube furnace and mounted on a TO8 header to provide the electrical connections to the heater and sensor electrode leads. This stand-alone prototype was tested in another enclosure with feedthroughs for both the sensor leads and the heater contacts. Power was applied to the resistive heater on the backside of the IDE substrate and increased until the baseline resistance of the sensor was the same as when measured with heat being externally supplied by the tube furnace. Approximately 2.8 watts of power was required to heat the sensor element to its target baseline resistance (19 MΩ). The performance of the sensor operating with an internal heater then was compared to that obtained with external heating. These data are presented in FIG. 9.

The performance of the sensor with internal heating was similar to the performance with external heating, although the response to 1% hydrogen was slightly greater and response was slightly slower when the sensor was tested with external heating. The slower response observed when testing with external heating was due to a much larger dead space in the quartz tube compared to the test fixture used once the sensor was mounted on the header and tested with the onboard heater. The loss in sensitivity can be explained by the kinetic difference of sensing heated gas versus sensing an ambient temperature gas. The tube furnace provided heat to both the sensor and the gases surrounding the sensor, while the resistive heater supplied heat only to the sensor and not to the surrounding gas.

Figure 10:
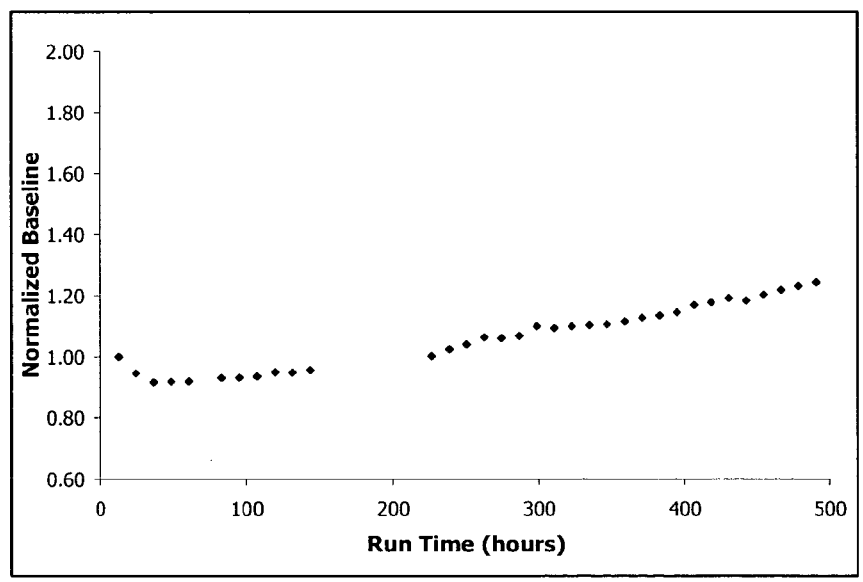
FIG. 10 is a graph of the long-term baseline resistance drift of the planar sensor of Example 19.
Figure 11:
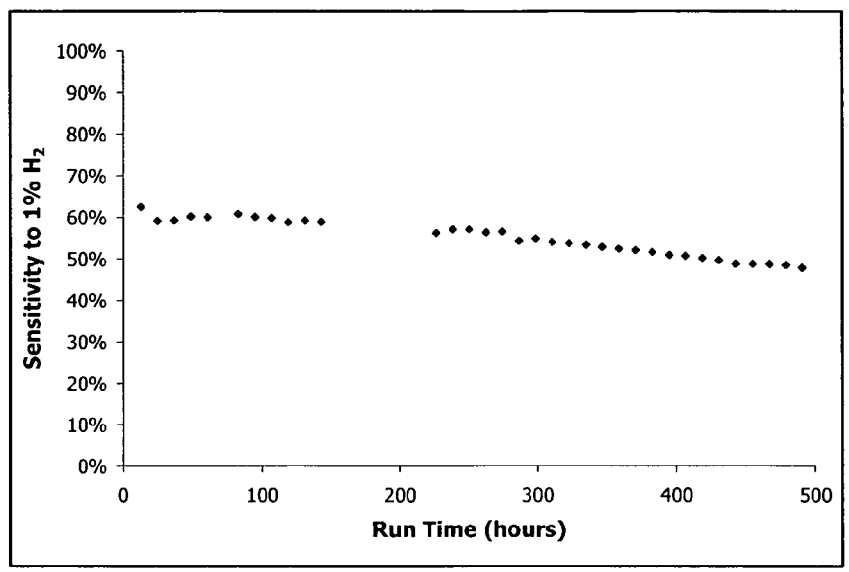
FIG. 11 is a graph of the long-term drift of hydrogen sensitivity of the planar sensor of Example 19.

Long-term tests were conducted on planar sensors to evaluate the stability of the baseline resistance and sensitivity during cycling in air between 0 and 1% $H_2$ (12-hour cycle times). These tests were conducted on a planar element, made through previously described methods, with external heat supplied by a tube furnace. Long-term stability data are presented in FIGS. 10 and 11. Over the course of this 500 hour test, the baseline resistance had increased by approximately 25 percent and the sensitivity had decreased from 60 to 48 percent for this planar sensor.

EXAMPLE 20

Tubular Hydrogen Sensor Element

Figure 13:
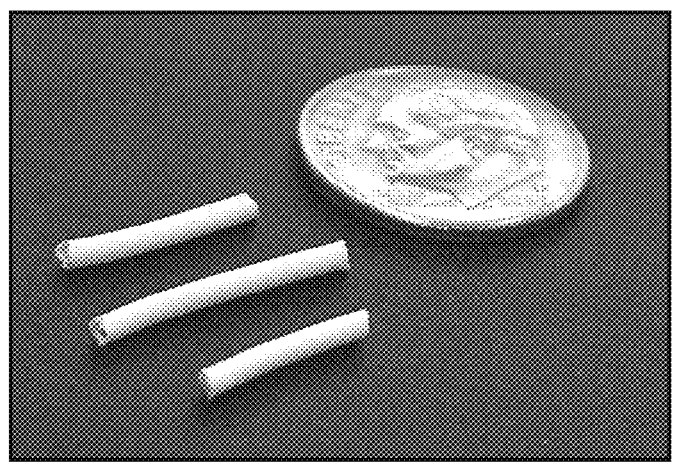
FIG. 13 is an image of exemplary sintered porous ceramic micro-tubes of the GDC (5% $SnO_2$) composition of Example 20.

Prototype micro-tubular sensors were fabricated, integrated with NiCr heaters, and tested for hydrogen sensitivity. A general schematic showing the manufacturing steps for the micro-tubular sensor elements is shown in FIG. 12. A 50-gram batch of the GDC (5% $SnO_2$) powder with a surface area of 14 $m^2$/gram was prepared for extrusion of support tubes. A thermal plastic dough was mixed using this composite material through the addition of conventional binders and plasticizers and extruded using a Bohlin Instruments RH2000 capillary rheometer. The tubes were dried and then sintered at 1100° C. The sintered micro-tubes had an approximate density of 65% theoretical. This density was considered to be in the ideal range for the sensor—sufficiently dense to provide mechanical ruggedness, yet sufficiently porous to provide a rough surface for optimum adhesion of subsequently deposited coatings. After sintering, the micro-tubes had an outside diameter of 1.5 mm and a wall thickness of 0.5 mm. The sintered tubes are shown in FIG. 13.

Figure 14:
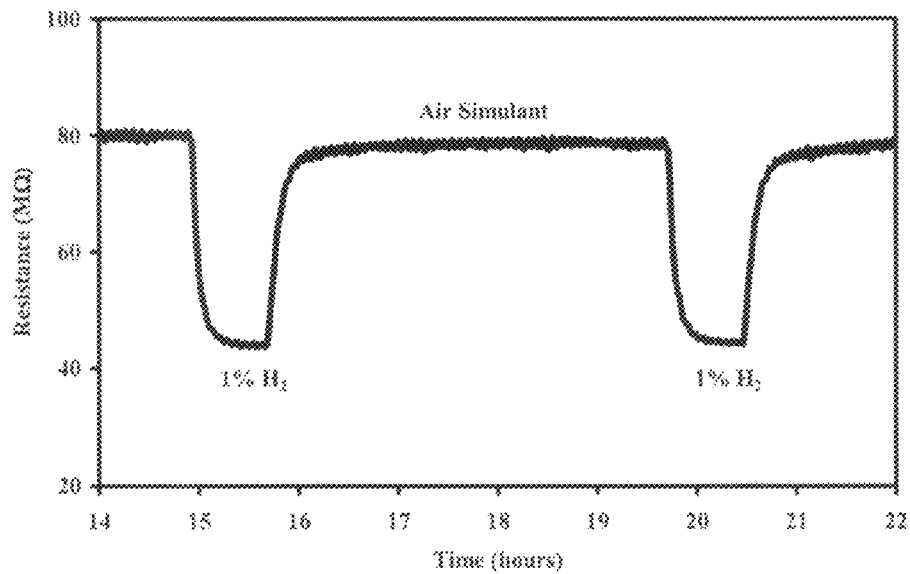
FIG. 14 is a graph of the hydrogen sensitivity of the tubular sensor element of Example 20 at 175° C.

Tubular sensors were fabricated from sintered 5% $SnO_2$-GDC tubes in the following manner: (1) silver lead wires were attached to the exterior of the tube using silver ink; (2) gold electrodes were painted on the tube, connected to the silver leads, and cured at 450° C. for 30 minutes; and (3) the sensor material was painted on the exterior of the tube and annealed at 800° C. for one hour. Performance of the tubular sensor elements (without internal heaters) was evaluated in a tube furnace using the same testing conditions as described above. The optimum operating temperature for the sensor was lowered from 300 to 200° C. (based on maximum sensitivity to 1% $H_2$). Testing of the sensor at temperatures as low as 175° C. still showed strong responses to 1% hydrogen, as shown in FIG. 14.

Figure 15:
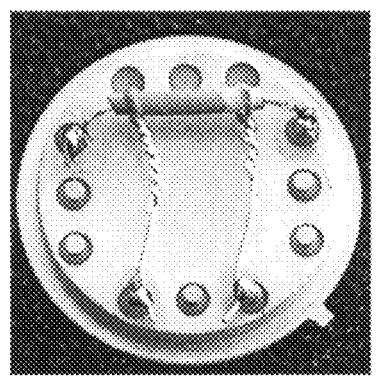
FIG. 15 is an image of an exemplary assembled micro-tubular hydrogen sensor prototype with internal heater as described in Example 20.

Multiple prototype tubular sensors were fabricated and tested. The internal heaters were made from 5Ω lengths of heater wire (34 AWG nichrome-60) by tightly coiling the wires. The coil heaters were designed so that the outside diameter of the coil would allow the heater to fit inside of the extruded micro-tube. A tubular sensor element is shown in FIG. 15. The performance of tubular prototype sensors was evaluated by applying various amounts of power to the internal heater and evaluating baseline resistance, $H_2$ sensitivity and cross-sensitivity using previously described methods. A heater power of only 750 mW was required to achieve a baseline resistance of 20 MΩ (corresponding to an estimated operating temperature of 200° C.), and only 615 mW of heater power was required to achieve a baseline resistance of 80 MΩ (corresponding to an estimated operating temperature of 175° C.). Sensor performance within this range of heater power exceeded that of the planar sensor of Example 19. Thus, the tubular structure reduced power consumption by more than 70 percent.

EXAMPLE 21

Tubular Hydrogen Sensor Elements with Alumina and YSZ Substrates

Figure 16:
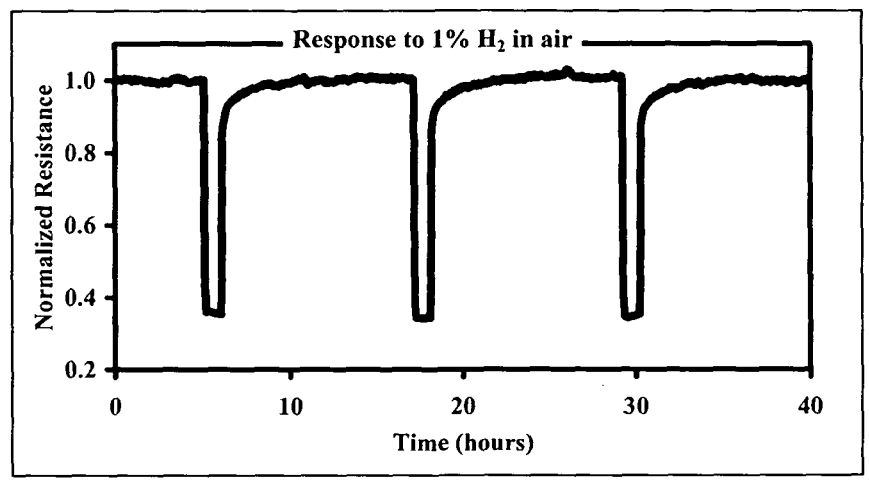
FIG. 16 is a graph of the hydrogen sensing performance of the micro-tubular sensor of Example 20.
Figure 17:
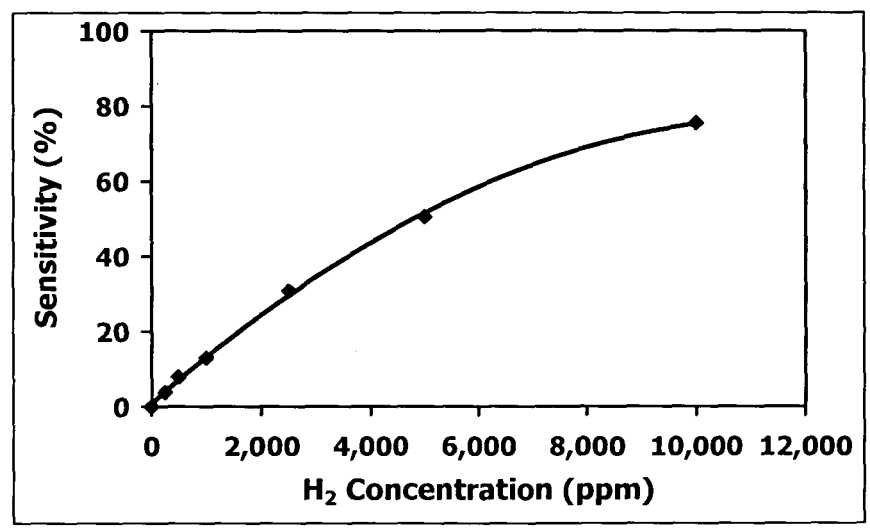
FIG. 17 is a graph of the quantitative response of the prototype tubular sensor of Example 20.

Purchased aluminum oxide and yttria (8 mol %) stabilized zirconia tubes were cut to 8 mm lengths. The alumina tubes had an outside diameter of 1 mm and wall thickness of 0.5 mm. The YSZ tubes had an outside diameter of 4.4 mm and wall thickness of 0.4 mm. Sensors were fabricated from these substrates using methods described in Example 20. Approximately 40Ω heater lengths were used for the alumina substrate sensors and approximately 10Ω lengths were used for the YSZ substrate sensors. The performance of the tubular sensor showed significant improvements over the planar sensor prototype of Example 19. An average response of greater than 60% was demonstrated when the sensor was exposed to one percent hydrogen in a dry simulated air background. This was a 50% improvement over the planar prototype. Data collected from three hydrogen cycles is shown in FIG. 16. The sensor exhibited quantitative responses over a range of hydrogen concentrations from 250 to 10,000 ppm, shown in FIG. 17.

The apparent response time of the tubular sensor also was improved over that of the planar prototype sensor of Example 19. The response time (or $t_{90}$) is defined as the time it takes for the signal of the sensor to reach 90% of the full response. The response time to 1% hydrogen of the planar prototype sensor of Example 19 was 2.3 minutes, whereas the response time for the tubular prototype sensor was only 20-30 seconds. Another key feature of the tubular sensor is its fast recovery time. The $t_{90}$ for the recovery of the sensor was less than 50 seconds.

Figure 18:
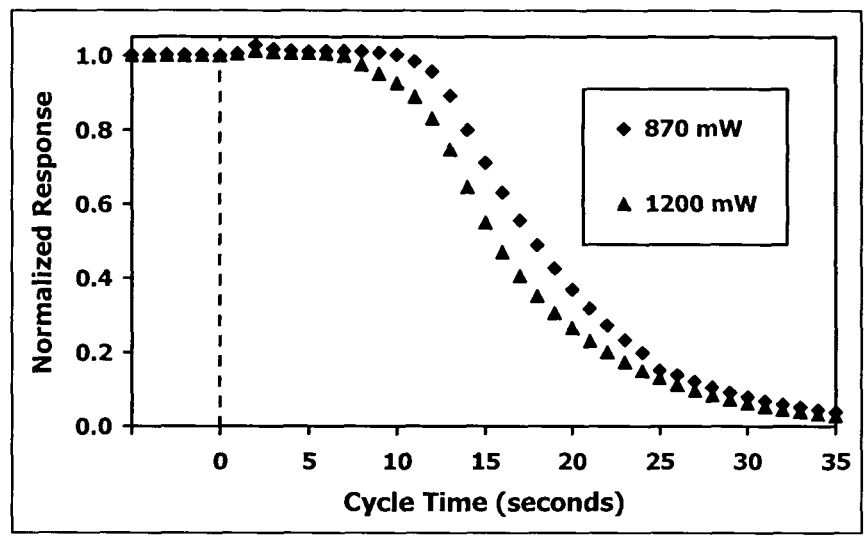
FIG. 18 is a graph of the effect of heater power (operating temperature) on response time of the micro-tubular sensor of Example 20.

FIG. 18 shows response times of the tubular sensor operating at different heater powers. Kinetics of the surface reactions increase as more power, or heat, is applied to the sensor, which was anticipated to decrease the response time of the sensor. There was a measurable decrease in sensor response time when operating the sensor at higher heater powers. After subtracting the seven second dead time, the $t_{90}$ for the sensor operated at 1200 mW was 20 seconds, compared to 23 seconds at 870 mW.

The tubular prototype sensor also exhibited the same interference resistance to both CO and $CH_4$ as described earlier. The sensor showed no response to $CH_4$ and only minimal movements in the baseline when exposed to 200 ppm CO. A plot of the raw data of the sensor signal appears in FIG. 19. The interference caused by the cross sensitivity to CO is not much greater than the noise in the baseline and could easily be tuned out by the sensor circuit design.

Figure 20:
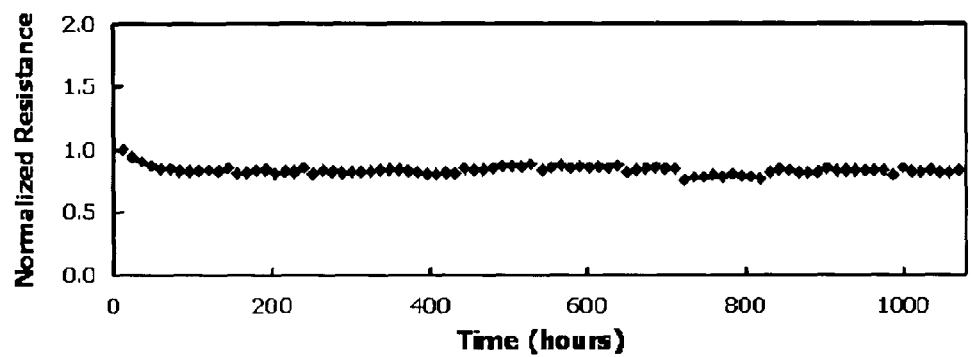
FIG. 20 is a graph of baseline resistance versus time for the micro-tubular hydrogen sensor of Example 20.
Figure 21:
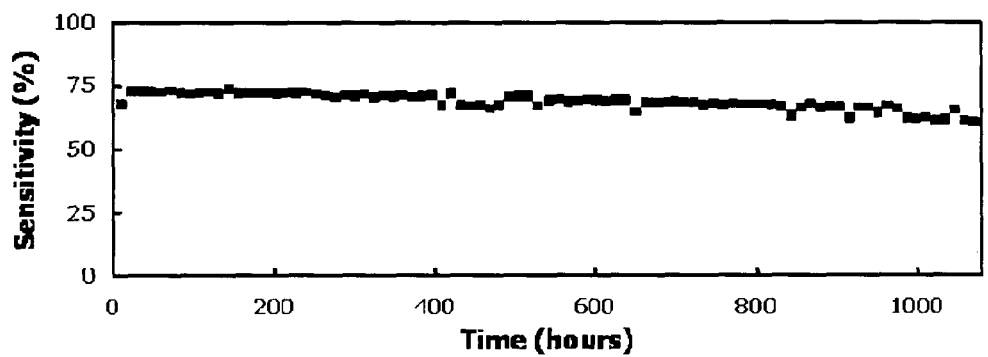
FIG. 21 is a graph of sensitivity to 1% $H_2$ versus time for the micro-tubular hydrogen sensor of Example 20.

A long-term test was completed for a tubular sensor, with results presented in FIGS. 20 and 21. These tests were conducted in a tube furnace at a controlled temperature of 200° C. The baseline resistance and sensitivity of the tubular sensor were remarkably stable over 600 hours of testing, with essentially no increase of baseline resistance or loss of sensitivity. The increased stability compared to planar sensors is due to the lower operating temperature of the tubular sensor (about 200° C. for the tubular sensor compared to about 300° C. for planar sensors). This would reduce aging effects, which typically occur via a thermally activated sintering mechanism. Sintering results in reduced gas accessibility to grain boundaries, which are the primary active sites for the sensor.

Figure 22:
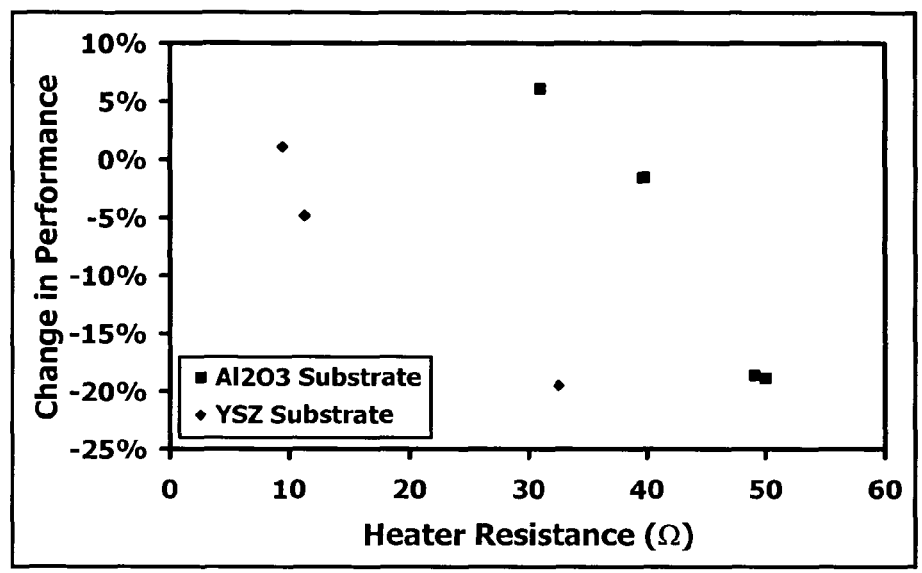
FIG. 22 is a graph of the change in sensor performance upon a change in relative humidity from 0% to 100% as a function of heater resistance for both aluminum oxide and yttria stabilized zirconia micro-tubular substrate sensors.
Figure 23:
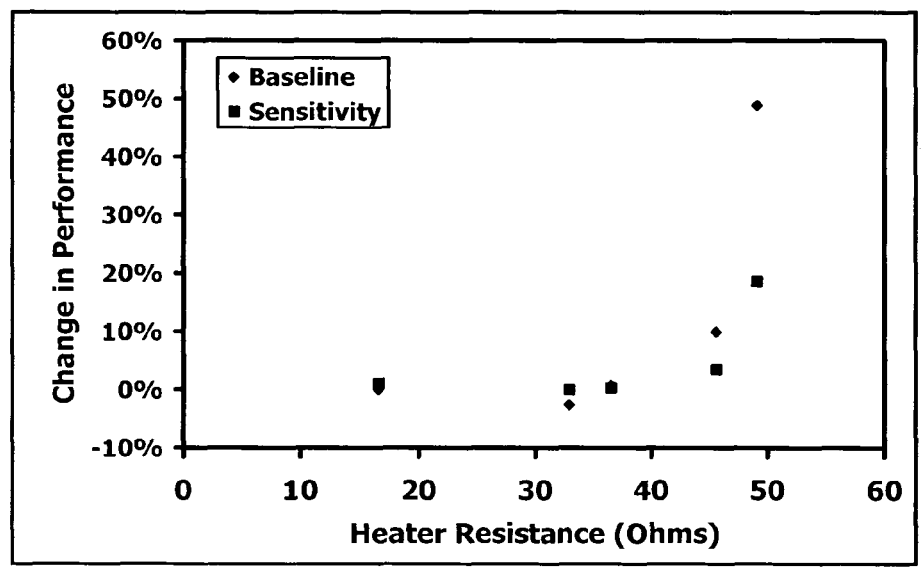
FIG. 23 is a graph of the change in sensor baseline resistance and sensitivity to 1% $H_2$ upon a change in relative humidity from 0% to 100% for aluminum oxide micro-tubular substrate sensors.
Figure 24:
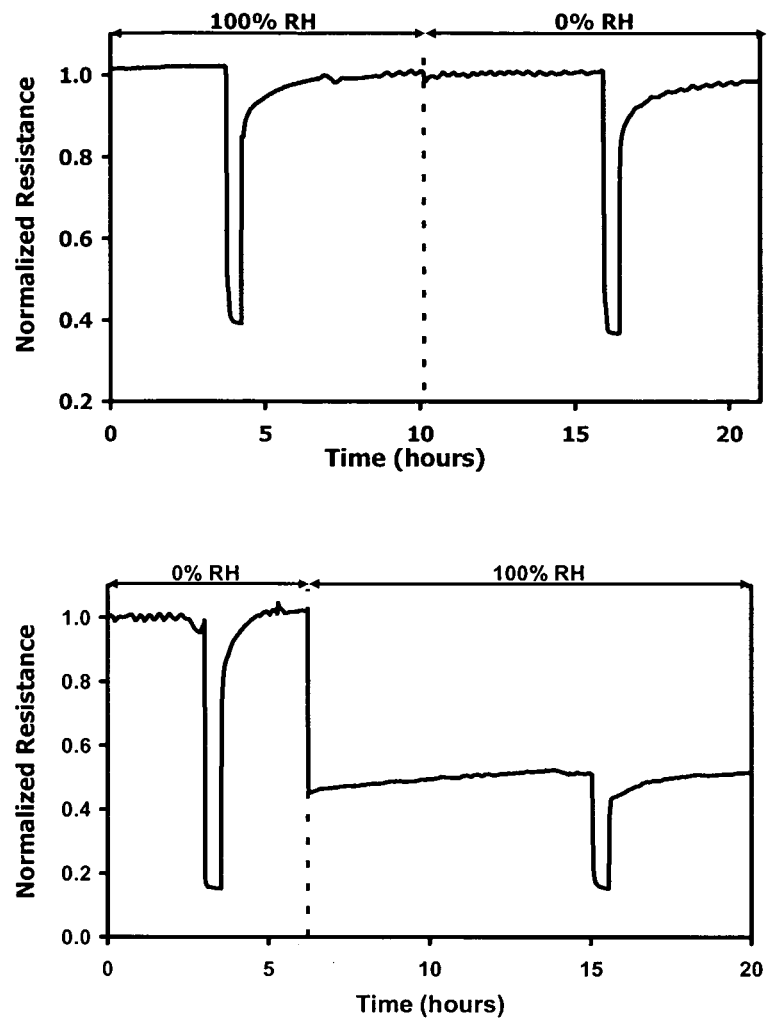
FIG. 24 is a graph of the response characteristics of an aluminum oxide micro-tubular substrate sensor with a 39.7Ω and a 49.1Ω heater upon a change in relative humidity from 0% to 100%.

Prototype tubular sensors were fabricated with varying heater resistance and tested for effects of relative humidity variation on sensor baseline resistance and sensitivity to hydrogen. Sensors were tested for sensitivity to 1% hydrogen in both dry (0% relative humidity) and wet (100% relative humidity) environments. The internal heaters were made from lengths of heater wire (40 AWG nichrome-60) by tightly coiling the wires. Heaters ranging from 30 to 50Ω were inserted into sensors with aluminum oxide tubular substrates. Heaters ranging from 9 to 35Ω were inserted into sensors with yttria stabilized zirconia (YSZ) tubular substrates. The coil heaters were designed so that the outside diameter of the coil would allow the heater to fit inside of the extruded micro-tube. FIG. 22 shows the effects of heater resistance on both baseline resistance and sensitivity to 1% hydrogen for both aluminum oxide and YSZ substrates. In the alumina oxide substrate sensors, heater resistance near 30Ω minimized the effects of humidity variation, while in the YSZ substrate sensors, much lower resistance heaters were required for the same humidity insensitivity. This relationship between heater resistance and humidity sensitivity was further explored by testing alumina substrate sensors with heaters as low as 15Ω (FIG. 23). A non-linear relationship was observed, with sensors having negligible sensitivity to humidity variation with heater resistance approximately less than 40Ω. With higher resistance heaters, humidity greatly impacted sensor performance. This effect is further illustrated in FIG. 24, showing the negligible effects of humidity on a 39.7Ω resistance heater sensor compared to the large humidity sensitivity of a 49.1Ω sensor.

Figure 25:
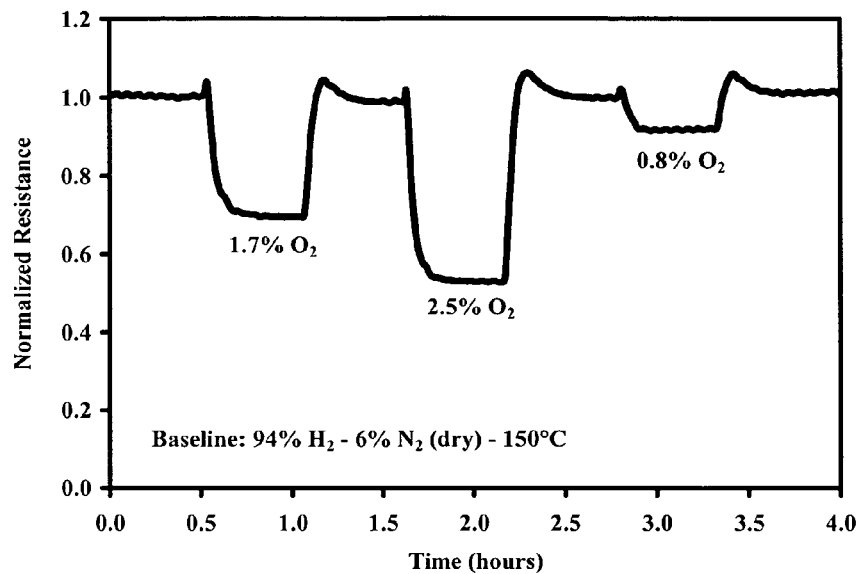
FIG. 25 is a graph of the quantitative detection of oxygen in hydrogen using the micro-tubular sensor of Example 20.

The micro-tubular sensor of this Example was also found to be useful in quantitatively detecting the presence of small amounts of oxygen in a hydrogen ambient (see FIG. 25). These data show that the sensor response with a high degree of sensitivity to varying oxygen concentrations in a hydrogen-rich background gas environment.

COMPARATIVE EXAMPLE

Commercial Chemical Resistor Type Hydrogen Sensor

The performance of the micro-tubular hydrogen sensor was compared to that of a commercially available chemical resistor type hydrogen sensor. The Figaro TGS 821 was selected for the comparison. The TGS 821 has a tin oxide ($SnO_2$) based ceramic sensing element and is heated by a small resistive heater. The tin oxide based sensor has a relatively high resistance in clean air, but its resistance decreases in the presence of a detectable gas. The TGS 821 was obtained and tested in accordance with documentation received with the sensor. The heater on the sensor operates at approximately 650 mW, which is similar to the micro-tubular sensor of Example 21.

Figure 19:
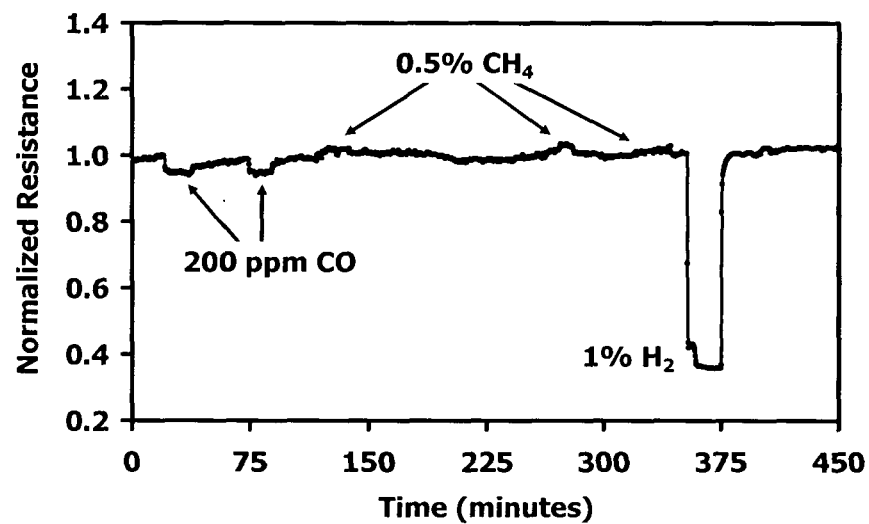
FIG. 19 is a graph of the interference resistance of the micro-tubular hydrogen sensor of Example 20.
Figure 26:
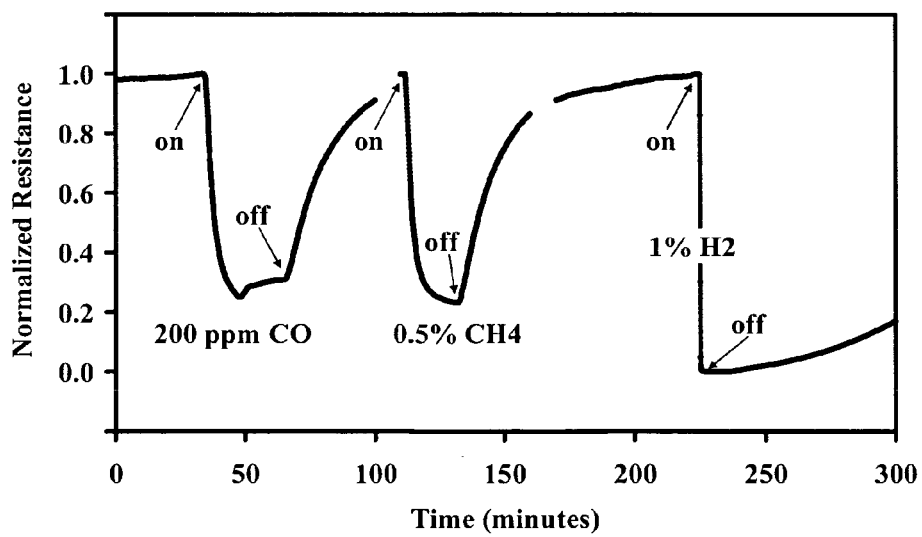
FIG. 26 is a graph of normalized responses of the sensor of the Comparative Example to 1% $H_2$, 200 ppm CO, and 0.5%.

The sensitivity of the TGS 821 sensor to 1% hydrogen matched the value reported in the product documentation. While the sensor was very sensitive to 1% hydrogen (greater than 99% response), it also showed very large responses to CO and $CH_4$ (see FIG. 26). The responses of 69% and 76% to 200 ppm CO and 0.5% $CH_4$, respectively, were consistent with values reported in the product documentation. In comparison, the sensor of Example 21 displayed negligible cross sensitivity to these concentrations of CO and $CH_4$ (FIG. 19).

Figure 27:
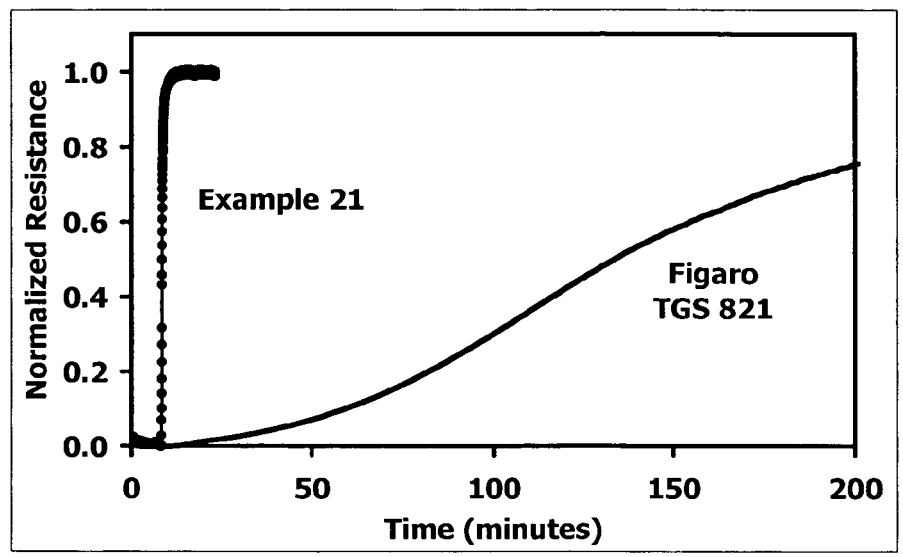
FIG. 27 is a graph of recovery times for the micro-tubular hydrogen sensor of Example 20 and the commercially available sensor of the Comparative Example.

Response times for both the TGS 821 sensor and the micro-tubular sensor of Example 21 were less than the application-specific target of thirty seconds (10 seconds for the TGS 821 sensor and 20 seconds for the micro-tubular sensor). However, the recovery time of the micro-tubular sensor was much faster, as shown in FIG. 27. The micro-tubular sensor recovered to its original baseline in 48 seconds after hydrogen was removed, while the TGS 821 sensor had not recovered to 70 percent of its original baseline resistance after three hours. Another advantage of the micro-tubular sensor is rapid startup time (less than 5 minutes). Start up of the TGS 821 sensor is slow—the product documentation states that the standard test conditions include a seven day pre-heating period before testing the sensor.

The use of the disclosed micro-tubular sensor design for hydrogen sensing is not limited by the use of the disclosed ceria-based sensor coating materials. The disclosed micro-tubular sensor element design can be used for a chemical resistor type hydrogen sensor using any known hydrogen sensitive oxide (such as tin oxide), hydrogen sensitive metal (such as palladium), hydrogen sensitive combination of oxide and metal, or any material that exhibits a measurable response (resistive and/or capacitive) to hydrogen. The geometry of the tubular support for the sensor can be varied over a wide range as long as the required tubular component can be manufactured.

Figure 28:
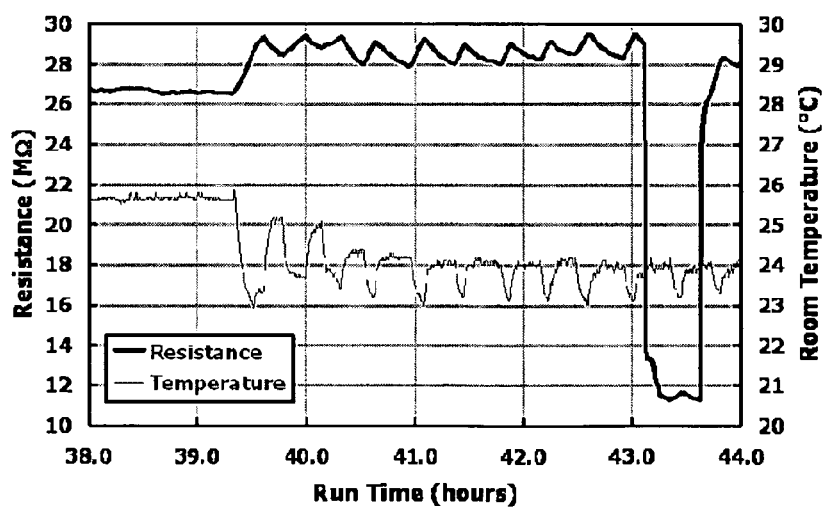
FIG. 28 is a graph of the effect of ambient temperature on the baseline resistance of the hydrogen sensor.

Although the above-described solid state ceramic sensor exhibits a fast response to hydrogen and minimal cross sensitivity to interfering gases, improvements may be needed before commercialization of the sensor so that the sensor may operate over a wide range of atmospheric conditions without the possibility of a false alarm. While testing sensor prototypes, the room temperature was found to have a significant effect on the baseline resistance of the sensor, as shown in FIG. 28, despite heating of the sensor to a temperature between 175° C. and 225° C. using a NiCr heater. The fluctuations in the room temperature due to the air conditioner cycling on and off can be directly correlated to movements in the baseline resistance. The large drop in resistance during hour 43 is a response of the sensor to 1.0% hydrogen. This observation is problematic because it means a shift in temperature could be detected as the presence of hydrogen. Even worse, a drop in the atmospheric temperature could increase the baseline resistance of the sensor and cause the presence of hydrogen to go undetected.

This temperature sensitivity issue could be solved by including a temperature sensor in a sensor control and alarm circuit. In this case, a calibration or look-up table would be required to correct for the temperature effect on the baseline sensor resistance.

Figure 29:
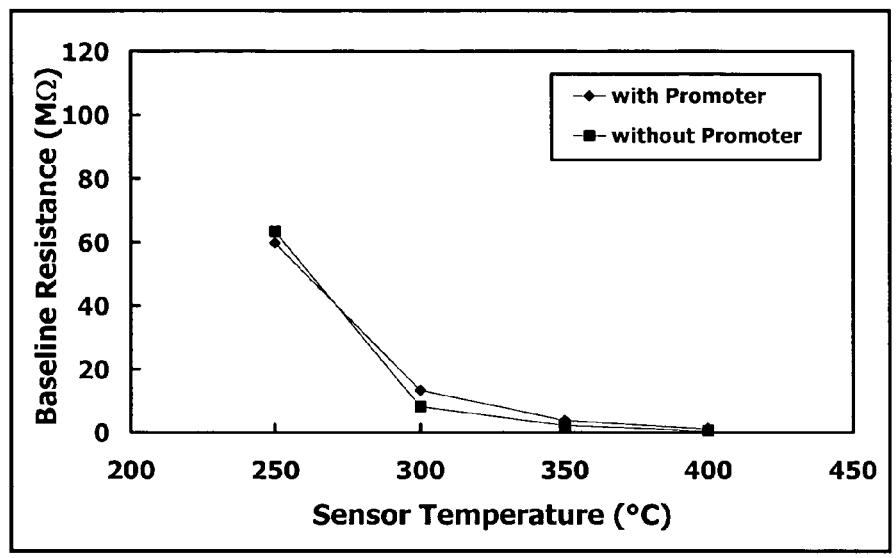
FIG. 29 is a graph of the effect of the promoter on the baseline resistance of the hydrogen sensor.

Alternatively, the difference in sensitivity between the sensor material with and without a promoter addition could be used to compensate for temperature variation, thus eliminating the need for a separate temperature sensor in the sensor control circuit. In this case, a dual sensor element having two sensors—an active (promoted) hydrogen sensor and an inactive (unpromoted) hydrogen sensor—is employed. As shown in FIG. 29, promoted and unpromoted sensors have the same baseline resistance over a range of temperatures and thus are affected by changes in the atmospheric temperature in the same way. The unpromoted sensor, however, has a significantly lower sensitivity to hydrogen than the promoted sensor (FIG. 6) so its response can be used for temperature compensation of the promoted sensor signal. This compensation could be implemented in a sensor control circuit through analog or digital methods including, for example, a Wheatstone bridge circuit, half-bridge Wheatstone bridge circuit, comparator circuit, or microprocessor.

In addition to providing built-in compensation for the effects of atmospheric temperature on the baseline, the dual sensor element may contribute to the overall stability of the sensor by canceling cross sensitivity. As described above, the addition of palladium to the sensor selectively increased the sensitivity to hydrogen relative to various cross sensitivities. While almost all of the cross sensitivity to CO and $CH_4$ can be tuned out by adjusting the operating temperature, the sensor still exhibits small changes in resistance in the presence of these gases. Because the palladium does not have much impact on those responses, both the promoted sensor and the unpromoted sensor would be expected to undergo similar changes in resistance in the presence of interfering gases such that these changes would be canceled out in an electronic control circuit.

Figure 30:
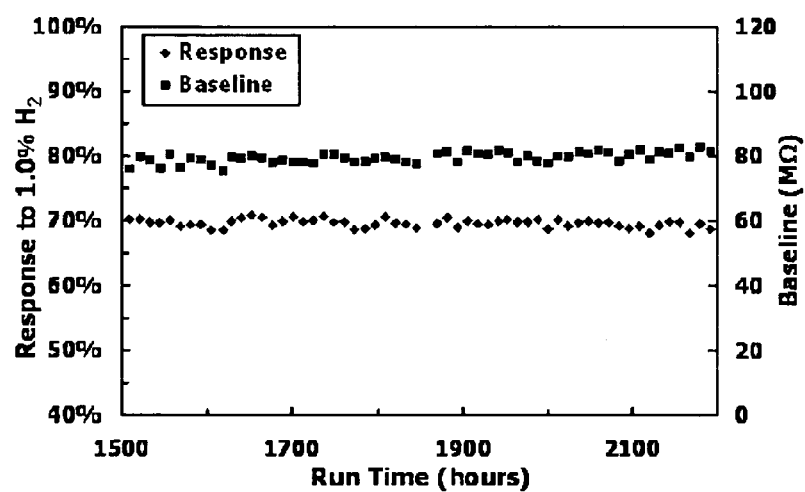
FIG. 30 is a graph of the zero and span drift of the hydrogen sensor of Example 20 at 175° C.

The dual sensor element also may contribute to the overall stability of the sensor by canceling zero drift. For example, when the sensor was operated at lower power levels (lower temperatures), a finite amount of baseline resistance drift was observed. FIG. 30 shows the final 700 hours of a long term test. After three months of testing, the drift in the baseline was less than $5 \times 10^{-3} M\Omega/hr$. It is assumed that the observed zero drift is an artifact of the ceramic sensor and not due to the palladium promoter. If this is the case, an unpromoted sensor would match the zero drift of the promoted sensor and serve to further stabilize the sensor signal.

One potential disadvantage of this approach is increased bulk and cost of the overall assembly as a result of adding the second, unpromoted sensor. Both the promoted and unpromoted sensors would have to be housed within the flame arrestor due to the elevated temperature of the NiCr heater. Potential solutions to this problem include reducing the size of the sensor elements through improved manufacturing capabilities or locating both the promoted and unpromoted sensors on the same tube support sharing a common electrode in the middle.

Yet another potential disadvantage of the dual sensor concept is the additional power required for two NiCr heaters. Both sensors would need to be heated, doubling the power requirements. However, reducing the size of the sensor elements and/or locating the promoted and unpromoted sensors on the same tube would reduce the power required.

Yet another potential disadvantage of the dual sensor concept is the need for consistency of baseline resistance from sensor to sensor. If part-to-part consistency cannot be achieved through optimization of manufacturing processes, an initial calibration of the baseline resistance of the promoted and unpromoted sensors may be required.

The tubular sensor device with dual sensor elements yields highly satisfactory results in combination with the hydrogen-sensitive composite material of the present invention. However, each element is expected to yield satisfactory results when used independently or in subcombinations of less than all of these elements. For example, the hydrogen-sensitive composite may be useful in devices having other than tubular configurations.

In addition, the tubular sensor device with dual sensor element may be useful with sensor coatings for detecting other gases, including but not limited to carbon monoxide, methane, hydrogen sulfide, sulfur oxides, nitrogen oxides, humidity, and ammonia. Such devices are expected to have improved baseline resistance if the gas sensor materials are susceptible to environmental effects.

The preferred embodiment of this invention can be achieved by many techniques and methods known to persons who are skilled in this field. To those skilled and knowledgeable in the arts to which the present invention pertains, many widely differing embodiments will be suggested by the foregoing without departing from the intent and scope of the present invention. The descriptions and disclosures herein are intended solely for purposes of illustration and should not be construed as limiting the scope of the present invention which is described by the following claims.

The invention claimed is:

1. A porous hydrogen selective composite material, comprising:
   a doped cerium oxide selected from the group consisting of zirconium-doped ceria, gadolinium-doped ceria, samarium-doped ceria, lanthanum-doped ceria, yttrium-doped ceria, calcium-doped ceria, strontium-doped ceria, and a mixture thereof;
   a modifier comprising tin oxide, indium oxide, titanium oxide, copper oxide, tungsten oxide, molybdenum oxide, nickel oxide, niobium oxide, or vanadium oxide; and a noble metal promoter comprising one or more of: palladium, ruthenium, platinum, gold, rhodium, and iridium.

2. The hydrogen selective composite material of claim 1, wherein the doped cerium oxide comprises one or more of: gadolinium-doped ceria and samarium-doped ceria.

3. The hydrogen selective composite material of claim 2, wherein the modifier comprises one or more of: tin oxide Of and indium oxide.

4. The hydrogen selective composite material of claim 1, wherein the modifier comprises one or more of: tin oxide and indium oxide.

5. The hydrogen selective composite material of claim 1, wherein the noble metal promoter comprises one or more of: palladium, ruthenium, and platinum.

6. The hydrogen selective composite material of claim 1, comprising at least about 1 wt % of the noble metal promoter.

7. The hydrogen selective composite material of claim 1, comprising at least about 1 wt % to about 94 wt % of the doped cerium oxide.

8. The hydrogen selective composite material of claim 1, comprising at least about 2.5 wt % of the modifier.

9. The hydrogen selective composite material of claim 1, wherein the modifier is present in an amount of at least about 5 wt %.

10. The hydrogen selective composite material of claim 1, wherein:
   the doped cerium oxide is gadolinium-doped ceria;
   the modifier comprises tin oxide and the modifier is present in an amount of at least about 5 wt %; and
   the noble metal promoter comprises palladium and the noble metal promoter is present in an amount of at least about 1 wt %.

11. The hydrogen selective composite material of claim 1, wherein:
   the doped cerium oxide is gadolinium-doped ceria;
   the modifier comprises indium oxide and the modifier is present in an amount of at least about 5 wt %; and
   the noble metal promoter comprises platinum and the noble metal promoter is present in an amount of at least about 1 wt %.

12. A hydrogen gas sensor device, comprising:
   a support;
   electrodes on a surface of the support; and
   a sensor coating on the electroded surface of the support, the sensor coating comprising a porous hydrogen selective composite material, wherein the hydrogen selective composite material comprises:
   a doped cerium oxide selected from the group consisting of zirconium-doped ceria, gadolinium-doped ceria, samarium-doped ceria, lanthanum-doped ceria, yttrium-doped ceria, calcium-doped ceria, strontium-doped ceria, and a mixture thereof;
   a modifier comprising one or more of: tin oxide, indium oxide, titanium oxide, copper oxide, cobalt oxide, tungsten oxide, molybdenum oxide, nickel oxide, iron oxide, niobium oxide, vanadium oxide, or another transition metal oxide; and
   a noble metal promoter comprising one or more of: palladium, ruthenium, platinum, gold, rhodium, and iridium.

13. The hydrogen gas sensor device of claim 12, wherein the support comprises one or more of: aluminum oxide, yttrium-stabilized zirconia, cerium oxide, gadolinium-doped ceria, magnesium aluminate, and magnesium oxide.

14. The hydrogen gas sensor device of claim 12, further comprising an integral resistive heater.

15. The hydrogen gas sensor device of claim 14, wherein the support is a micro-tubular support and the resistive heater is in the interior of the support.

16. The hydrogen gas sensor device of claim 14, wherein the resistance of the heater is operable to control the sensitivity of the sensor device to relative humidity.

17. The hydrogen gas sensor device of claim 14, wherein the support is planar and the resistive heater is on the support surface opposite the electroded surface.

18. The hydrogen gas sensor device of claim 12, wherein the doped cerium oxide of the hydrogen selective composite material comprises one or more of: gadolinium-doped ceria and samarium-doped ceria.

19. The hydrogen gas sensor device of claim 12, wherein the modifier of the hydrogen selective composite material comprises one or more of: tin oxide and indium oxide.

20. The hydrogen gas sensor device of claim 12, wherein the noble metal promoter comprises one or more of: palladium, ruthenium, and platinum.

21. The hydrogen gas sensor device of claim 12, wherein the noble metal promoter is present in an amount of at least about 1 wt %.

22. The hydrogen gas sensor device of claim 12, wherein the modifier is present in an amount of at least about 2.5 wt %.

23. The hydrogen gas sensor device of claim 12, wherein the modifier is present in an amount of at least about 5 wt %.

24. The hydrogen gas sensor device of claim 12, wherein:
   the doped cerium oxide is gadolinium-doped ceria;
   the modifier comprises tin oxide and the modifier is present in an amount of at least about 5 wt %; and
   the noble metal promoter comprises palladium and the noble metal promoter is present in an amount of at least about 1 wt %.

25. The hydrogen gas sensor device of claim 12, wherein:
   the doped cerium oxide is gadolinium-doped ceria;
   the modifier comprises indium oxide and the modifier is present in an amount of at least about 5 wt %; and
   the noble metal promoter comprises platinum and the noble metal promoter is present in an amount of at least about 1 wt %.

26. A gas sensor device, comprising:
   a support;
   electrodes on a surface of the support; and
   a sensor coating on the electroded surface of the support, the sensor coating comprising a porous hydrogen selective composite material, wherein the hydrogen selective composite material comprises:
   about 1 wt % to about 94 wt % of a doped cerium oxide the doped cerium oxide comprising one or more of: zirconium-doped ceria, gadolinium-doped ceria, samarium-doped ceria, lanthanum-doped ceria, yttrium-doped ceria, calcium-doped ceria, or strontium-doped ceria;
   a modifier comprising one or more of: tin oxide, indium oxide, titanium oxide, copper oxide, cobalt oxide, tungsten oxide, molybdenum oxide, nickel oxide, iron oxide, niobium oxide, vanadium oxide, or another transition metal oxide; and
   a noble metal promoter comprising one or more of: palladium, ruthenium, platinum, gold, rhodium, and iridium.

27. The gas sensor device of claim 26, wherein the support comprises one or more of: aluminum oxide, yttrium-stabilized zirconia, cerium oxide, gadolinium-doped ceria, magnesium aluminate, and magnesium oxide.

28. The gas sensor device of claim 26, further comprising an integral resistive heater.

29. The gas sensor device of claim 28, wherein the support is a micro-tubular support and the resistive heater is in the interior of the support.

30. The gas sensor device of claim 28, wherein the resistance of the heater is operable to control the sensitivity of the sensor device to relative humidity.

31. The gas sensor device of claim 28, wherein the support is planar and the resistive heater is on the support surface opposite the electroded surface.

32. The gas sensor device of claim 26, wherein the doped cerium oxide of the hydrogen selective composite material comprises one or more of: gadolinium-doped ceria and samarium-doped ceria.

33. The gas sensor device of claim 26, wherein the modifier of the hydrogen selective composite material comprises one or more of: tin oxide and indium oxide.

34. The gas sensor device of claim 26, wherein the noble metal promoter comprises one or more of: palladium, ruthenium, and platinum.

35. The gas sensor device of claim 26, wherein the noble metal promoter is present in an amount of at least about 1 wt %.

36. The gas sensor device of claim 26, wherein the modifier is present in an amount of at least about 2.5 wt %.

37. The gas sensor device of claim 26, wherein the modifier is present in an amount of at least about 5 wt %.

38. The gas sensor device of claim 26, wherein:
the doped cerium oxide is gadolinium-doped ceria;
the modifier comprises tin oxide and the modifier is present in an amount of at least about 5 wt %; and
the noble metal promoter comprises palladium and the noble metal promoter is present in an amount of at least about 1 wt %.

39. The gas sensor device of claim 26, wherein:
the doped cerium oxide is gadolinium-doped ceria;
the modifier comprises indium oxide and the modifier is present in an amount of at least about 5 wt %; and
the noble metal promoter comprises platinum and the noble metal promoter is present in an amount of at least about 1 wt %.

* * * * *